(12) United States Patent
Eckhardt et al.

(10) Patent No.: US 6,730,113 B2
(45) Date of Patent: May 4, 2004

(54) METHOD AND APPARATUS FOR STERILIZING OR DISINFECTING A REGION THROUGH A BANDAGE

(75) Inventors: Richard Eckhardt, Arlington, MA (US); Geoffrey H. Jenkins, Wellesley Hills, MA (US); Sandra Kimball, Boston, MA (US)

(73) Assignee: UV-Solutions LLC, Wellesley, MA (US)

(*) Notice: Subject to any disclaimer, the term of this patent is extended or adjusted under 35 U.S.C. 154(b) by 0 days.

(21) Appl. No.: 10/173,129

(22) Filed: Jun. 17, 2002

(65) Prior Publication Data

US 2003/0031586 A1 Feb. 13, 2003

Related U.S. Application Data

(60) Provisional application No. 60/298,790, filed on Jun. 15, 2001, provisional application No. 60/300,803, filed on Jun. 15, 2001, provisional application No. 60/316,744, filed on Aug. 31, 2001, and provisional application No. 60/334,722, filed on Oct. 31, 2001.

(51) Int. Cl.[7] .................................................. A61N 5/06
(52) U.S. Cl. ............................ 607/94; 128/898; 604/20
(58) Field of Search .......................... 604/20, 49, 289, 604/290, 304, 305; 607/94; 128/898

(56) References Cited

U.S. PATENT DOCUMENTS

| | | | |
|---|---|---|---|
| 4,006,534 A | | 2/1977 | Coffman |
| 4,182,050 A | | 1/1980 | Righi |
| 4,239,041 A | | 12/1980 | Popovich et al. |
| 4,464,336 A | | 8/1984 | Hiramoto |
| 4,469,835 A | | 9/1984 | Laurin |
| 4,475,900 A | | 10/1984 | Popovich et al. |
| 4,503,333 A | | 3/1985 | Kulin et al. |
| 4,620,845 A | | 11/1986 | Popovich et al. |
| 4,727,868 A | * | 3/1988 | Szycher et al. ............... 602/43 |
| 4,806,770 A | | 2/1989 | Hylton et al. |
| 4,868,397 A | | 9/1989 | Tittle |
| 4,877,964 A | | 10/1989 | Tanaka et al. |
| 4,909,254 A | * | 3/1990 | Wilkinson .................... 607/94 |
| 4,910,942 A | | 3/1990 | Dunn et al. |
| 4,950,902 A | | 8/1990 | Ritter |
| 4,952,369 A | | 8/1990 | Belilos |
| 4,973,847 A | | 11/1990 | Lackey et al. |
| 5,023,460 A | | 6/1991 | Foster, Jr. et al. |
| 5,104,392 A | | 4/1992 | Kittrell et al. |
| 5,126,572 A | | 6/1992 | Chu |
| 5,144,146 A | | 9/1992 | Wekhof |
| 5,185,532 A | | 2/1993 | Zabsky et al. |
| 5,193,544 A | | 3/1993 | Jaffe |
| 5,240,675 A | | 8/1993 | Wilk |
| 5,260,020 A | | 11/1993 | Wilk et al. |
| 5,292,312 A | * | 3/1994 | Delk et al. .................. 604/180 |
| 5,344,419 A | | 9/1994 | Spears |
| 5,498,394 A | | 3/1996 | Matschke |
| 5,567,616 A | | 10/1996 | Dill, II |
| 5,597,597 A | | 1/1997 | Newman |
| 5,607,419 A | | 3/1997 | Amplatz et al. |
| 5,614,151 A | | 3/1997 | LeVay et al. |
| 5,637,877 A | | 6/1997 | Sinofsky |
| 5,671,314 A | | 9/1997 | Gregory et al. |
| 5,695,482 A | | 12/1997 | Kaldany |
| 5,758,660 A | * | 6/1998 | Lokken ....................... 128/877 |
| 5,760,407 A | * | 6/1998 | Margosiak et al. ........ 250/461.2 |
| 5,786,598 A | | 7/1998 | Clark et al. |
| 5,788,940 A | | 8/1998 | Cicha et al. |
| 5,855,203 A | | 1/1999 | Matter |
| 5,871,522 A | * | 2/1999 | Sentilles ....................... 607/94 |
| 5,892,233 A | | 4/1999 | Clement |
| 5,898,277 A | | 4/1999 | Farnsworth et al. |
| 5,920,075 A | | 7/1999 | Whitehead |
| 5,925,885 A | | 7/1999 | Clark et al. |
| 5,961,870 A | | 10/1999 | Hogan |
| 5,996,155 A | | 12/1999 | Chao et al. |
| 6,087,781 A | | 7/2000 | Leppelmeier |
| 6,090,346 A | | 7/2000 | Rose et al. |
| 6,096,264 A | | 8/2000 | Peifer |
| 6,132,784 A | | 10/2000 | Brandt et al. |
| 6,165,526 A | | 12/2000 | Newman |
| 6,297,047 B1 | | 10/2001 | Butts |
| 6,379,614 B1 | | 4/2002 | Sergio et al. |

FOREIGN PATENT DOCUMENTS

| | | | |
|---|---|---|---|
| EP | 0 925 793 A2 | 6/1999 | |
| EP | 1033138 A1 | * 9/2000 | ............. A61L/2/10 |
| GB | 2 301 272 A | 11/1996 | |

OTHER PUBLICATIONS

"Derma–Wand Germicidal UVC Lamp", National Biological Corporation, Form No. DW–1, Dec. 1998.
ROVA UV Toothbrush Sterilizer for Homeuse, for a New Sanitary Life, RD–930 Toothbrush Sterilizer Ultraviolet (UV), RoadPia Brand! pp. 1–2, Jei Corporation, printed Feb. 27, 2000.
Test Result RD–930 RoadPia UV Toothbrush Sterilizer, pp. 1–2, Jei Corporation, printed Feb. 27, 2000.

* cited by examiner

Primary Examiner—Roy D. Gibson
Assistant Examiner—H M. Johnson, III
(74) Attorney, Agent, or Firm—Wolf, Greenfield & Sacks, P.C.

(57) ABSTRACT

Methods and apparatus for sterilizing or disinfecting a region through a bandage. One embodiment of the invention is directed to a method, comprising acts of determining the transmissivity of at least a portion of a bandage to ultraviolet light, and selecting an intensity of ultraviolet light to be applied through at least a portion of the bandage. Another embodiment of the invention is directed to a method of sterilizing or disinfecting a region underneath a bandage on a patient. A further embodiment of the invention is directed to an apparatus for sterilizing or disinfecting a region of tissue of a patient. The apparatus comprises an ultraviolet light-emitting lamp and a bandage adapted to transmit at least some of the ultraviolet light emitted by the lamp. Another embodiment of the invention is directed to a bandage, comprising an ultraviolet light-transmissive film, and a color-changing material coupled to the film to indicate an exposure of the film to ultraviolet light.

17 Claims, 19 Drawing Sheets

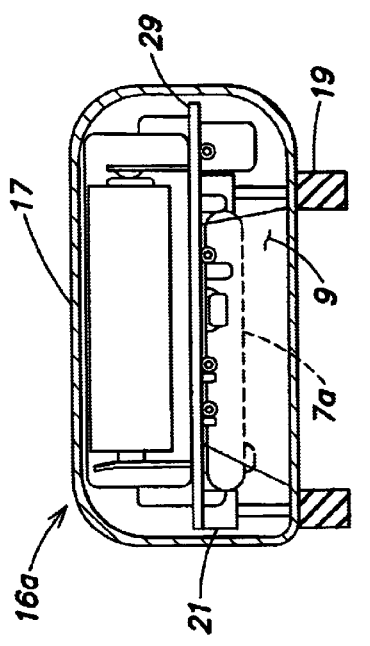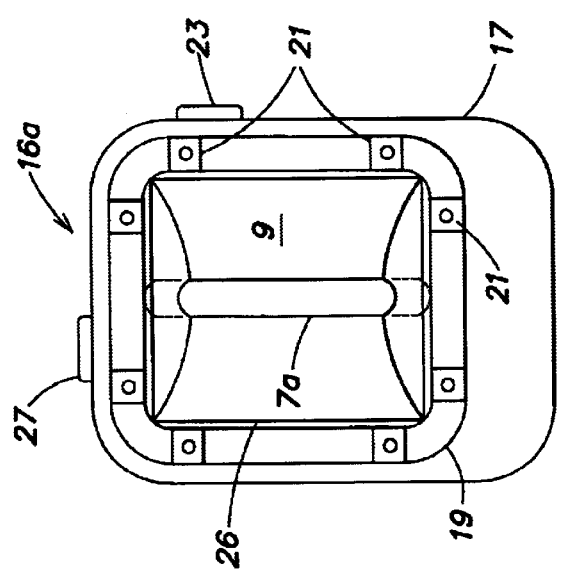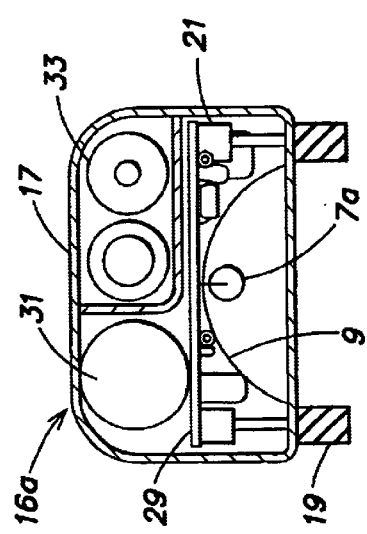

METHOD AND APPARATUS FOR STERILIZING OR DISINFECTING A REGION THROUGH A BANDAGE

PRIORITY CLAIM

This application claims the benefit, under 35 U.S.C. §119(e), of the filing date of: U.S. provisional application Ser. No. 60/298,790 entitled "Method and Apparatus for Disinfecting Catheters and Entrance Sites," filed Jun. 15, 2001; U.S. provisional application Ser. No. 60/300,803 entitled "Method and Apparatus for Disinfecting Catheters and Entrance Sites," filed Jun. 15, 2001; U.S. provisional application Ser. No. 60/316,744 entitled "Method and Apparatus for Disinfecting Wound Sites," filed Aug. 31, 2001; and U.S. provisional application Ser. No. 60/334,722 entitled "Method and Apparatus for Disinfecting Catheter Entrance Sites with a Dressing," filed Oct. 31, 2001; which are incorporated herein by reference.

FIELD OF THE INVENTION

The present invention relates generally to the field of sterilization or disinfection systems and methods.

BACKGROUND OF THE INVENTION

Infection is a primary concern in health care settings. Bacteria and other potentially harmful microbes can generate infections when they enter the body through wounds, catheter entrance sites, and other openings in the body, thereby bypassing the body's natural defenses. Infections, often absent at the time of admission to a hospital, are a serious source of morbidity, mortality, and excess cost in health care settings.

Catheters, a frequent conduit into the body for microorganisms, are typically sterilized before insertion into the body. Further, regions of skin that are or will be breached are typically treated with antiseptic or germicidal chemicals. As evidenced by the continued high rate of infection of catheter entrance sites and/or wounds, it is clear that the present techniques for sterilizing these regions are inadequate.

While ultraviolet radiation has been used for the sterilization of disinfection of objects in some applications, ultraviolet light has long been associated with skin cancer, sunburns, and other harmful skin effects. Common wisdom and practice has encouraged the non-exposure of skin to ultraviolet radiation.

SUMMARY OF THE INVENTION

One embodiment of the invention is directed to a method of sterilizing or disinfecting a region underneath a bandage on a patient. The method comprises an act of applying ultraviolet light to the region through the bandage.

Another embodiment of the invention is directed to an apparatus for sterilizing or disinfecting a region of tissue of a patient. The apparatus comprises an ultraviolet light-emitting lamp and a bandage adapted to transmit at least some of the ultraviolet light emitted by the lamp. The bandage covers at least a portion of the region of tissue.

A further embodiment of the invention is directed to a method, comprising acts of determining the transmissivity of at least a portion of a bandage to ultraviolet light, and selecting an intensity of ultraviolet light to be applied through at least a portion of the bandage. Another embodiment of the invention is directed to a bandage, comprising an ultraviolet light-transmissive film and a color-changing material coupled to the film to indicate an exposure of the film to ultraviolet light.

A further embodiment of the invention is directed to a device for use with a catheter inserted at an entrance site through skin of a patient. The device comprises a component having a conduit to retain the catheter and space the catheter from the skin of the patient near the entrance site, wherein the component is located and shaped such that the component assists in forming a substantially air-tight seal between the skin and a bandage adhered to at least a part of the component.

Another embodiment of the invention is directed to a device for use with a catheter inserted at an entrance site through skin of a patient. The device comprises a component having a conduit to retain the catheter and space the catheter from the skin of the patient near the entrance site, wherein the component is located and shaped such that the component assists in forming a substantially light-tight seal between the skin and a bandage adhered to at least a part of the component.

A further embodiment of the invention is directed to a method of using an ultraviolet-transmissive bandage. The method comprises acts of applying the bandage over skin of a patient, and applying ultraviolet light through the bandage to the skin.

BRIEF DESCRIPTION OF THE DRAWINGS

FIGS. 3 and 4A–4E illustrate an instantaneous sterilization/disinfection unit;

FIGS. 10A–9C illustrate a further embodiment of a UV-transmissive bandage;

DETAILED DESCRIPTION

As mentioned above, ultraviolet light is potentially harmful to the skin. Consequently, many individuals take precautions against exposure. Because of its perceived dangerous nature, ultraviolet light has not been contemplated for the sterilization or disinfection of skin, including wounded skin and healthy skin, or catheter entrance sites.

In view of the foregoing, one aspect of the present invention is directed to a method and apparatus for sterilizing or disinfecting a region of tissue and/or a catheter entrance site of a patient using ultraviolet (UV) light. A region of tissue to be sterilized or disinfected may include unbreached skin, such as a region where a surgical incision is to be made, or breached skin, such as a wound site or a catheter entrance site. In the case where a catheter entrance site is being sterilized or disinfected, a portion of the catheter in the vicinity of the entrance site may also be sterilized. Another aspect of the invention is directed to a method and apparatus for sterilizing or disinfecting a region of tissue and/or a catheter entrance site of a patient using UV light transmitted through a bandage.

It should be appreciated that while the terms "sterilize" and "disinfect" are used generally herein, the methods and apparatus described may be used to achieve a desired level (e.g., low or high) of sterilization or disinfection. The sterilization or disinfection may occur by killing microorganisms, inactivating microorganisms (i.e., rendering the microorganisms unable to reproduce), or any combination thereof. It should further be appreciated that, according to the present invention, a region of tissue or a catheter entrance site to be sterilized or disinfected may be that of either a person or an animal.

Sterilization or Disinfection of Tissue and/or an Inserted Catheter

Figure 1:
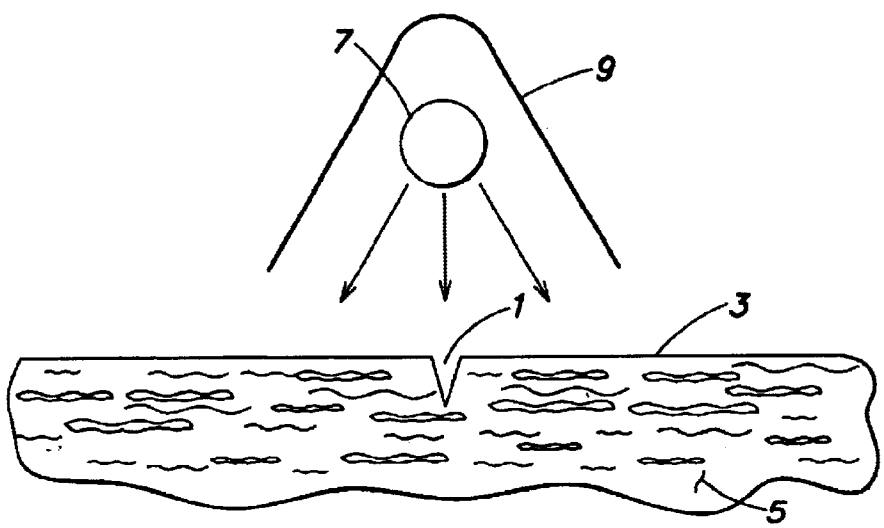
FIG. 1 illustrates a method for sterilizing or disinfecting a region of skin or tissue with a light source.

FIG. 1 illustrates a method for sterilizing or disinfecting a region of skin or tissue of a patient using sterilizing or disinfecting light, in accordance with one embodiment of the invention. Sterilizing or disinfecting light is emitted by a light source 7 and exposed to wound 1 and/or surrounding tissue 5. Tissue 5 includes skin 3 and tissue below the surface of skin 3. While skin 3 is highly attenuating to sterilizing or disinfecting light, some light may permeate to the tissue below skin 3, for example exposing pores of skin 3. A reflector 9 is disposed near light source 7 to aid in directing light emitted by light source 7 towards wound 1 and surrounding skin 3. While reflector 9 is shown as disposed above light source 7, it may be located on either side of the light source 7 or may be eliminated entirely. Further, additional reflectors may be included around light source 7 in accordance with the invention. Light source 7 may be any light source that emits light capable of sterilization or disinfection. For example, light source 7 may be an ultraviolet (UV) light source such as a mercury vapor lamp, a xenon flash lamp, a continuous arc lamp, UV light emitting diodes (LEDs), a UV laser, or any other solid state or non-solid state UV light-emitting device. The lamp may emit narrow spectrum light (e.g., a line spectrum) or broad spectrum light. Broad spectrum light may include, e.g., UVA, UVB, and UVC light, or UV light accompanied by light from another portion of the electromagnetic spectrum. For example, the emission of both UV and visible light from light source 7 may enhance the effectiveness of the light source, as the sensitivity of different microorganisms to light varies with the wavelength of the light. It should be appreciated that though a single light source 7 is described and illustrated, one or more light sources may be used.

Light may be generated by light source 7 in one or more flashes. If multiple flashes are generated, the flashes may be applied at specified intervals that may occur, for example, one or more times per day. A flash lamp or other non-continuous lamp may be used to generate light in one or more flashes. The lamp may be a high intensity source of sterilizing or disinfecting light where the sterilization dosage may be applied in less than a few minutes or seconds. The energy of a single flash may be sufficient to deliver a sterilizing or disinfecting dosage, e.g., greater than 10 mJ/cm$^2$ of UVC, to all surfaces to be sterilized or disinfected.

Light may also be generated by light source 7 as continuous radiation over a period of time. To generate continuous radiation, a lower intensity source capable of emitting sterilizing or disinfecting light continuously over a period of time may be used. The intensity of the light emitted by light source 7 may be adjusted for use on skin of varying sensitivity to ultraviolet light. For example, the light emitted by light source 7 may be controlled at a lower intensity if the sterilization of disinfection method is performed on an infant, for whom a lower intensity may be more appropriate.

Wound 1 may be a lesion, cut, abrasion, or sore sustained by the patient. Alternatively, wound 1 may be an incision or puncture created by a healthcare professional. The method described above may also be applied to unbreached skin, in accordance with the invention. For example, the method for sterilizing skin 3 and/or tissue 5 of a patient using sterilizing or disinfecting light may be used to sterilize or disinfect the skin at a penetration site prior to a medical procedure that breaches the skin. Thus, the method described in connection with FIG. 1 may be employed by medical professionals prior to or after medical procedures that breach the skin. The method may also be employed by consumers or medical professionals to treat the skin after accidental breach of the skin.

Figure 2:
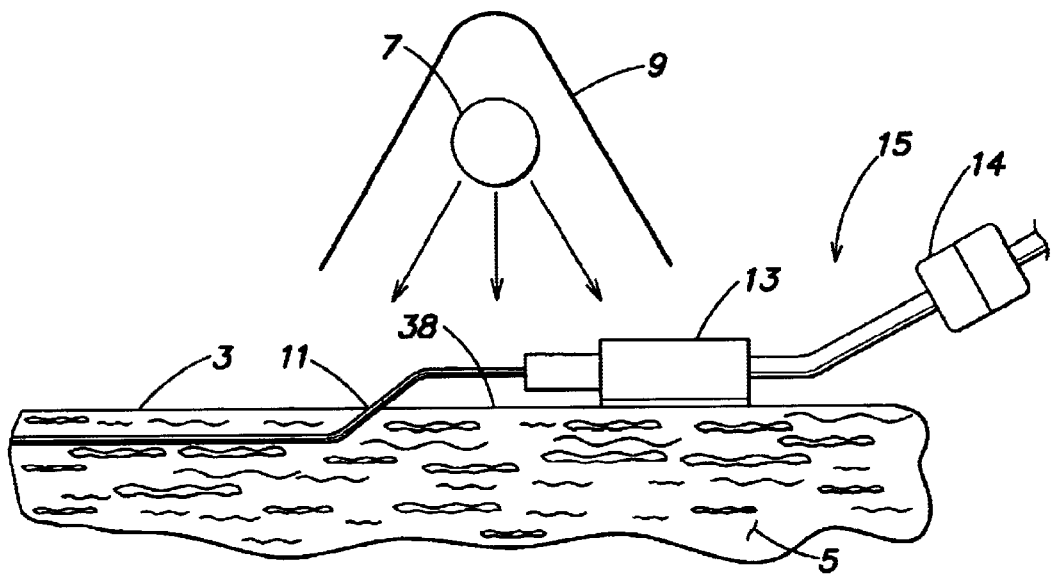
FIG. 2 illustrates a method for sterilizing or disinfecting a catheter entrance site with a light source.

FIG. 2 illustrates a method for sterilizing an installed catheter and/or surrounding skin of a patient using sterilizing or disinfecting light. Sterilizing or disinfecting light is emitted by a light source 7, which directs light towards an entrance site 11 of a catheter 15 and/or the catheter itself in the vicinity of entrance site 11. Entrance site 11 includes the opening in skin 3 through which the catheter passes. Entrance site 11 may also include skin 3 and tissue 5 surrounding the opening. Reflector 9 may have any of the configurations described in connection with FIG. 1. Further, light source 7 may have any of the configurations described in connection with FIG. 1, and may be operated in any of the described modes.

As shown in FIG. 2, catheter 15 includes a hub 13 and a connector 14. Hub 13, which is external to the patient, may be any junction where two or more lumens, each having separate tubing, merge into a single multi-lumen tube. Connector 14 may be a mechanism for attaching and detaching catheter 15 from external catheter equipment (e.g., a bag containing intravenous fluid). It should be appreciated that the catheter illustrated in FIG. 2 is just one example of a catheter that may be sterilized or disinfected in accordance with the invention. As described herein, a catheter may include any conduit through which fluids or mechanical devices pass into or out of the body. For example, a standard injection needle, a blood sample needle, a cannula, a trocar sheath, an introducer, or a shunt may be considered a catheter. A device that breaches the skin may also be considered a catheter. For example, a heart catheter, an endoscope, or a laparoscope may be considered a catheter. The catheter need not pass through an opening in the skin; instead the catheter may pass through a natural opening, as is the case with Foley catheters or other urinary catheters. In the above cases, the catheter passes through the body's natural barrier to microorganisms, and thus renders it susceptible to infection.

Instantaneous Sterilization or Disinfection

Figure 3:
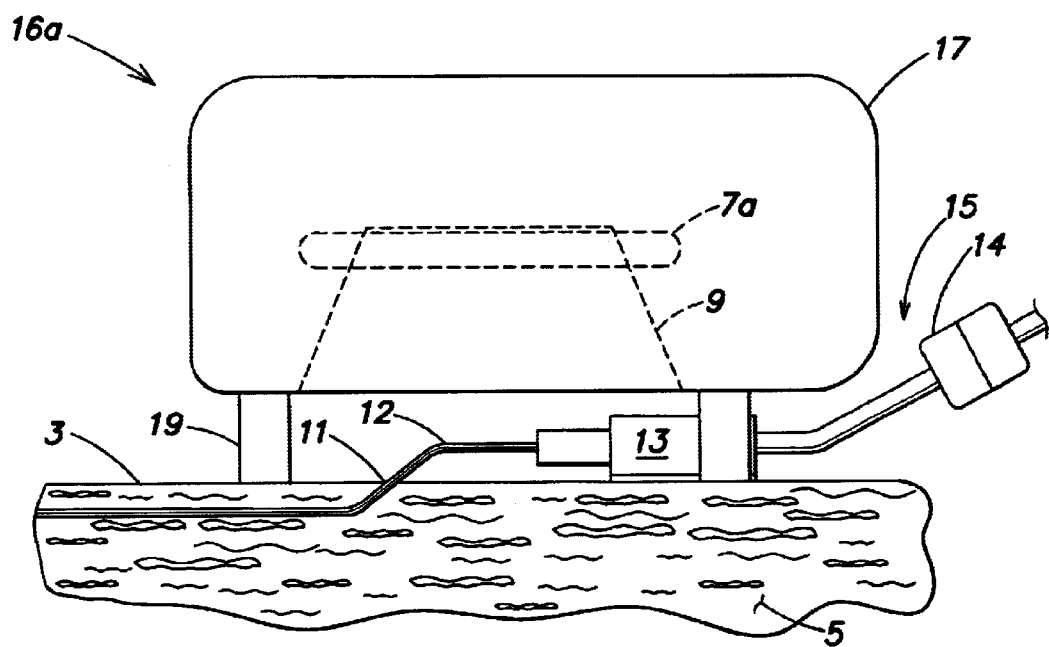
Figure 4E:
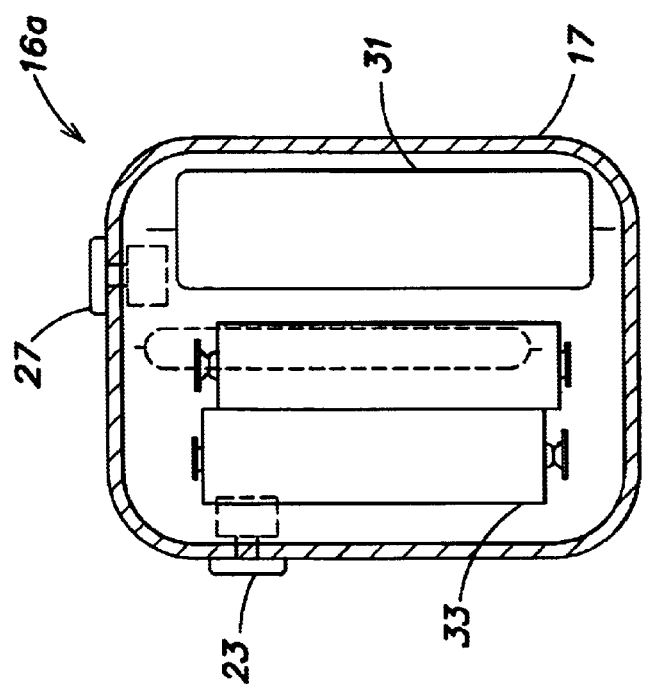
Figure 4D:
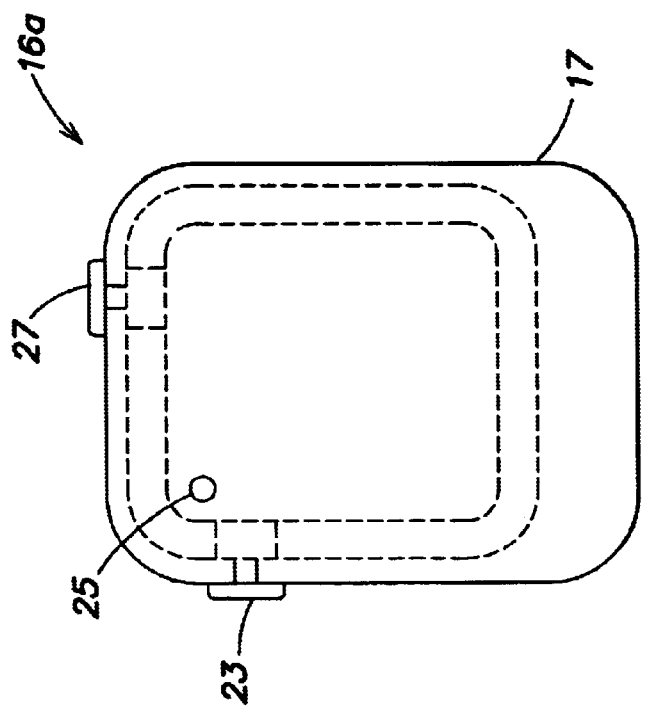

FIGS. 3 and 4A–4E illustrate an instantaneous sterilization/disinfection unit 16a adapted to generate one or more light flashes, in accordance with one embodiment of the invention. As shown in FIG. 3, a housing 17 encloses a flash light source 7a and reflector 9. Reflector 9, disposed about flash light source 7a, causes light emitted by flash light source 7a to be reflected at range of angles, thereby minimizing shadowing of the skin under catheter 15.

Flash light source 7a and reflector 9 are optionally protected by a UV transmissive window or screen (not shown) in an opening 26 at the bottom of the unit. The window may be made from quartz, fused silica, a UV transmissive glass or a screen, or a perforated sheet of metal or other material. In some applications, it is desirable to limit the amount of UVA, UVB, visible, infrared light, and/or portions of the UVC spectrum emitted, for example for use on sensitive skin or on infants susceptible to sunburn or local overheating. In this case, an optical filter may be incorporated into the window or the light source envelope to absorb or block undesired wavelengths. Alternatively, a dichroic mirror, which passes, rather than reflects the undesired wavelengths, may be used. A window or mirror may also include a textured surface or other diffusing mechanism to alter the exit angle of light and thereby reduce shadowing.

A light seal 19 is disposed around opening 26 in instantaneous sterilization/disinfection unit 16a. When light seal 19 is pressed against a patient or an object, it creates a substantially light-tight chamber to contain the light emitted by flash light source 7a and prevent injury or discomfort to the user or others nearby. Thus, the light emitted by flash light source 7a is substantially confined to housing 17 and the region on the patient surrounded by light seal 19. This region may include a region of skin 3 or tissue 5 and a region of catheter 15 near entrance site 11.

Light seal 19 may be formed from a complaint material. For example, light seal 19 may be formed from a convoluted and/or foamed opaque elastomeric material such as neoprene, natural rubber, silicone rubber, or a thermoplastic elastomer (TPE). The use of a compliant material allows a substantially light-tight chamber to be formed when light seal 19 of instantaneous sterilization/disinfection unit 16a is placed over an irregularly shaped surface. For example, light seal 19 may conform to a body, a bandage, tape, or a catheter and its components. In FIG. 3, a portion of light seal 19 conforms to the shape of hub 13 of catheter 15. The compliance of light seal 19 also allows instantaneous sterilization/disinfection unit 16a to be placed over catheter 15 for sterilization/disinfection without disconnecting catheter 15 at connector 14 from external catheter equipment. However, the external catheter equipment may be disconnected at connector 14 to allow hub 13 and connector 14 of catheter 15 to fit under instantaneous sterilization/disinfection unit 16a, within the confines of light seal 19, during sterilization or disinfection.

Instantaneous sterilization/disinfection unit 16a may be used to sterilize or disinfect entrance site 11 prior to insertion of catheter 15 to prevent the transport of microorganisms from skin 3 to tissue 5 during insertion of the catheter, or may be used while catheter 15 is in place. Instantaneous sterilization/disinfection unit 16a may also be used prior to penetration of skin 3 at the location of entrance site 11. Instantaneous sterilization/disinfection unit 16a may be used in addition to, or instead of, chemical treatment of skin 3 with a chemical sterilizer or disinfectant, e.g., prior to incision of skin 3 at entrance site 11. Sterilization or disinfectant chemicals may include germicidal or antiseptic chemicals such as alcohol, iodine, or betadine.

Instantaneous sterilization/disinfection unit 16a may contain safety interlock actuators 21 coupled to light seal 19 to prevent accidental activation of flash light source 7a when the unit is not properly positioned. Safety interlock actuators 21 detect the compression of light seal 19 at one or more locations (e.g., six as shown in FIG. 4C) to verify that light seal 19 is placed against a surface before flash light source 7a is allowed to trigger. An alternate or additional safety interlock may be included to prevent flash light source 7a from triggering unless the interior of housing 17 contains substantially no light, indicating that the light seal between the interior and exterior of housing 17 is substantially complete. A photodetector (not shown) in housing 17 may be used to detect the presence of light in housing 17.

As noted previously, instantaneous sterilization/disinfection unit 16a is adapted to generate light flashes. To generate light flashes, light source 7 may be a xenon flash lamp, and may be made with an envelope of quartz, fused silica, or UV transparent glass to maximize the output of UV light in the flash. Flash light source 7a may be driven with a high current density, e.g., 3,000 to 6,000 amps/cm$^2$, and a short flash duration, e.g., less than 200 microseconds for a small flash unit, for maximum UVC light production. The energy required by flash light source 7a to generate a flash sufficient for sterilization or disinfection is determined by the amount of area to be illuminated, the minimum sterilizing light dosage desired, the uniformity of the illumination, and the spectrum of flash light source 7a. For example, a flash light source made from UV glass used to illuminate 25 square centimeters (about 4 square inches) produces a UVC energy intensity of about 20 mJ/cm$^2$ and a total flash input energy of about 20 joules. Flash light source 7a may also generate UVA, UVB, infrared, and visible light.

Instantaneous sterilization/disinfection unit 16a includes a circuit board 29 enclosed within housing 17. Circuit board 29 may include a capacitor 31 for storing a charge used by flash light source 7a to generate a flash, and circuitry to charge the capacitor and control the charging and flashing. Circuit board 29 is also coupled to a power source and safety interlock circuitry to prevent accidental triggering at inappropriate times. The circuitry required to charge the capacitor and trigger the flash may be the same as that used in typical photographic flash units, which is well known in the industry. One example of circuitry that may be included on circuit board 29 will be discussed in connection with FIGS. 16 and 17.

Housing 17 includes a power switch 23 to initiate the charging of capacitor 31. Power switch 23 may be a simple on-off power switch or pushbutton to control the power to circuit board 29 to charge capacitor 31. Power switch 23 is coupled to a power source, which is shown as batteries 33 in FIGS. 4A, 4B, and 4E. Batteries advantageously allow instantaneous sterilization/disinfection unit 16a to be portable and hand-held. Further, the power requirement for a typical sterilization/disinfection unit is such that several hundred of more sterilization/disinfection operations may be performed using a single set of batteries. However, external power from an AC power source may also be used. Housing 17 also includes a trigger switch 27 to control activation of flash light source 7a when safety interlock actuators, when present, are activated. Power switch 23 and/or trigger switch 27 may be manipulated manually (e.g., by pressing a button), or may be coupled to one or more actuators 21 in light seal 19 to trigger upon depression of light seal 19. The inclusion of power switch 23 and trigger switch 27 enhances the safety of instantaneous sterilization/disinfection unit 16a and reduces its power consumption. However, either of power switch 23 or trigger switch 27 may be eliminated, as they are not necessary to the operation of the unit.

A UV dosage control mechanism may also be included to vary the intensity of the UV light generated by flash light source 7a. For example, the UV light intensity may be varied to compensate for the application of UV light through a bandage, which will be discussed in connection with FIG. 12, or to account for the sensitivity of the patient's skin. The UV dosage control may be continuously variable or variable in discrete steps determined by a switch. The sterilizing light output is controlled by altering the energy stored in capacitor 31 by changing the voltage to which capacitor 31 is charged, or by switching one or more capacitors into the circuit to change the total capacitance value.

A ready indicator 25, such as a light emitting diode (LED) may be included on the external surface of housing 17 to alert an operator when the charging of capacitor 31 is complete, and hence when a flash may be generated by flash light source 7a. A second indicator (not shown), or a color change or flashing of a light of indicator 25, may be included to alert an operator that safety interlock actuators 21 have been activated, and hence that instantaneous sterilization/disinfection unit 16a unit may be operated. A third indicator (not shown), or a change in color or flashing of other indicators, may be used to indicate that a successful flash has occurred.

Instantaneous sterilization/disinfection unit 16a, described above, is just one exemplary apparatus for sterilizing or disinfecting a catheter, a catheter entrance site, a wound, and/or a region of skin using one or more light flashes. Those skilled in the art will readily see many possible variations on the physical configuration, electronic circuitry, and controls of instantaneous sterilization/disinfection unit 16a described above, which are intended to fall within the scope of the invention.

Continuous Process Sterilization or Disinfection

Figure 5A:
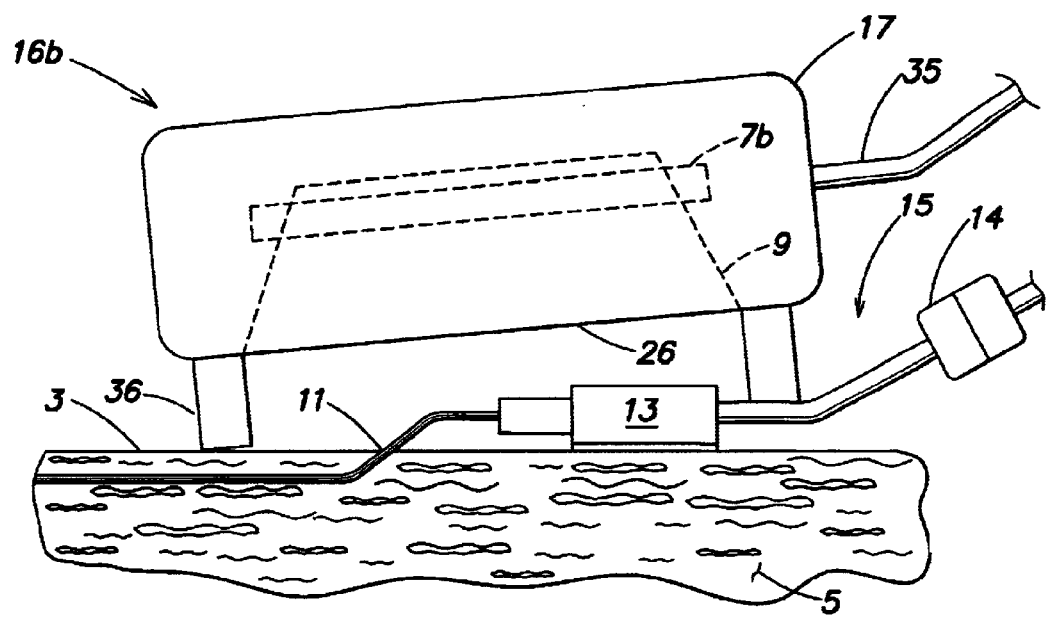
FIGS. 5A–5C illustrate a continuous process sterilization/disinfection unit.
Figure 5B:
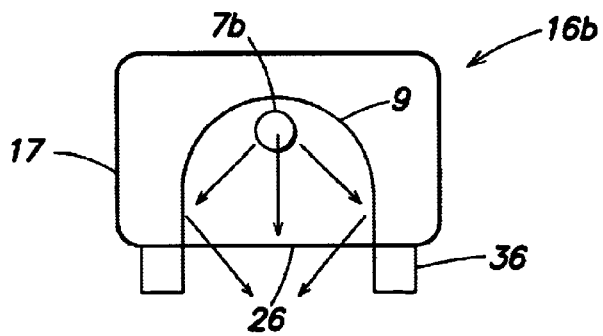
Figure 5C:
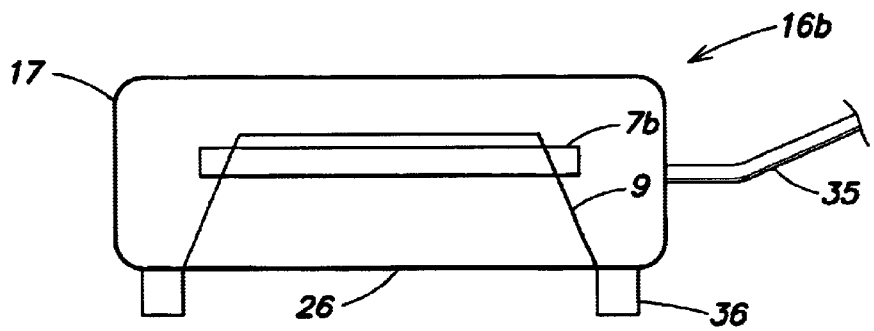

FIGS. 5A–5C illustrate a continuous process sterilization/disinfection unit 16b adapted to generate continuous radiation for a period of time, in accordance with one embodiment of the invention. Continuous process sterilization/disinfection unit 16b operates on the same principles as instantaneous sterilization/disinfection unit 16a, except that light is generated by a continuous light source 7b at a lower intensity and over a longer period of time.

As shown in FIG. 5A, continuous process sterilization/disinfection unit 16b operates by positioning the unit over catheter 15 near entrance site 11, such that it illuminates entrance site 11 and surrounding skin 3 and/or tissue 5, as well as a portion of catheter 15 near entrance site 11. Continuous process sterilization/disinfection unit 16b is maintained in this position for a time sufficient to provide a sterilizing or disinfecting dosage of UV light. The sterilization may be completely continuous, or it may be intermittent and repeated at regular intervals as desired.

For convenience, continuous process sterilization/disinfection unit 16b may include a mechanism for attaching the unit to a site to be sterilized/disinfected or a location near to the site, although the unit may be hand-held. For example, adhesive tape or straps with fasteners such as hook-and-loop fasteners (i.e., Velcro) may be used. The straps with fasteners may be looped around a portion of the body or fastened to bandages, etc. that are already attached to the body. Housing 17 may include receptacles or fastening points for the straps. Alternatively, adhesive tape, straps, or another attachment mechanism may be used to attach continuous process sterilization/disinfection unit 16b to catheter 15. Since the light seal for continuous process sterilization/disinfection unit 16b is not critical, a primary advantage of attaching the unit is to hold the unit in the proper position for sterilization or disinfection.

If tape or bandages are used over entrance site 11, they may be removed before sterilization or disinfection. If UV-transmissive tape and bandages are used, they may be left in place with the sterilization/disinfection unit placed over them, as will be discussed in connection with FIG. 13. Continuous process sterilization/disinfection unit 16b is designed to allow for its use over catheter 15 without disconnecting the catheter from the external circuit. Alternatively, the external catheter circuit may be disconnected to allow hub 13 and connector 14 of catheter 15 to fit beneath continuous process sterilization/disinfection unit 16b.

As shown, a housing 17 of continuous process sterilization/disinfection unit 16b encloses continuous light source 7b and reflector 9, and is coupled to a power cord 35. Reflector 9 reflects light from continuous light source 7b to the surfaces and objects to be sterilized or disinfected. Reflector 9 also serves to redirect the light so that it strikes the surfaces and objects from a multitude of angles, thereby minimizing shadows and providing more uniform illumination.

Because the overall power requirement for continuous process sterilization/disinfection unit 16b tends to be higher than for instantaneous sterilization/disinfection unit 16a, it is preferable to power the unit using AC power transmitted via a power cord 35, although in some applications batteries may be appropriate. To minimize the size and weight of the unit when batteries are used, it is preferable, but not necessary, to locate the batteries in a remote location connected by a power cord. Operator controls, such as an on-off switch and controls for a timer are preferably small and light-weight enough to be included in housing 17, although they may be remotely located at the other end of the power cord. Further, in the example of FIGS. 5A–5C, continuous process sterilization/disinfection unit 16b includes a base 36 rather than a compliant light seal because the lower intensity of the light generated by instantaneous sterilization/disinfection unit 16a does not present as much of a safety concern, although precautions may still be appropriate to minimize exposure of the eyes to the UV light.

Because a lower intensity of sterilizing or disinfecting light is required for continuous process sterilization/disinfection unit 16b, as discussed above, continuous light source 7b may be a standard germicidal mercury vapor lamp. These lamps produce most of their energy at a wavelength of approximately 253.7 nanometers, in the middle of the UVC sterilizing band. With a mercury vapor lamp, continuous process sterilization/disinfection unit 16b may require several minutes or more for sterilization or disinfection. Mercury vapor lamps produce a small amount of energy at UV wavelengths outside of the UVC band, as well as energy in the visible spectrum. The intensity of UVA and UVB light produced by these lamps is low and typically does not present a hazard for others nearby at the dosage level required for periodic sterilizations or low-level, long-term, continuous sterilization.

If the intensity of the UV light at skin 3 is low enough, continuous light source 7b maybe illuminated for long periods of time (e.g., hours or days) without damage to skin 3. Commonly available mercury vapor lamps typically produce an intensity incompatible with continuous operation, unless the light level is attenuated with an optical filter or the electrical drive to continuous light source 7b is controlled to reduce the intensity of the emitted light. A reduction in the intensity of the light output may be accomplished by turning continuous light source 7b alternately on and off. The alternation may be performed at a low frequency (e.g., with a period of a few seconds or minutes), or at a high frequency (e.g., with a period of less than a second). The alternation may also be performed at a low (less than 50%) or high (greater than 50%) duty cycle. The switching of power to continuous light source 7b may be performed with an electronic circuit, a mechanical timer, or electromechanically, all of which are well known to those skilled in the art.

Alternatively, sterilization or disinfection operations may be performed once a day or a few times a day, and continuous light source 7b may be turned on for long enough to perform a complete sterilization or disinfection operation for each instance. The timing for each operation may be preformed by a standard timer or with a light sensor that measures light exposure and turns continuous light source 7b off when a desired dosage is reached. Continuous process sterilization/disinfection unit 16b may also be turned on and off manually by an operator.

A UV dosage control may be included in continuous process sterilization/disinfection unit 16b, to compensate for the application of UV light through a bandage, which will be discussed in connection with FIG. 13, or to account for the sensitivity of the patient's skin. The UV dosage control may be continuously variable or variable in discrete steps determined by a switch. As discussed above, the sterilizing light output is controlled by altering the intensity of light emitted by continuous light source 7b, the duty cycle of continuous light source 7b, or the total on-time for each sterilization or disinfection.

A UV transparent window (not shown), made of a material such as quartz, fused silica, or UV transparent glass, may be included at opening 26 to protect continuous light source 7b while allowing light to reach the target surfaces. The window could include an optical filter to alter the spectrum of the emitted light. This may result in a spectrum having greater efficacy and/or less damaging light. The window could also include a textured surface or other diffusing mechanism to alter the exit angle of the emitted light and thereby reduce shadowing of the targets.

The drive circuitry for continuous light source 7b of continuous process sterilization/disinfection unit 16b is included in housing 17. The circuitry is not shown here, as it is typically the same as that used for standard visible fluorescent lamps and is well known to those skilled in the art.

Continuous process sterilization/disinfection unit 16b, described above, is just one exemplary apparatus for sterilizing or disinfecting a catheter, a catheter entrance site, a wound, or a region of skin using a continuous application of radiation. Those skilled in the art will readily see many possible variations on the physical configuration, electronic circuitry, and controls of continuous process sterilization/disinfection unit 16b described above, which are intended to fall within the scope of the invention. For example, continuous light source 7 may be replaced by a pulse light source that requires a number of pulses over a period of time to provide the required dosage. Continuous light source 7 may be replaced by a broad-spectrum light source to provide other wavelengths of light along with UV light. Optical filters or dichroic mirrors may be incorporated into continuous process sterilization/disinfection unit 16b to alter the spectrum of the outputted light by reducing the intensity of damaging wavelengths of light.

Sterilization or Disinfection Using a Light Directing Component

For complete sterilization of catheter 15 near entrance site 11, it is desirable for all points on catheter 15 near entrance site 11 to be exposed to the appropriate dosage of sterilizing light. Further, to prevent microorganisms from entering the body at entrance site 11, it is desirable that entrance site 11 and surrounding skin 3 be sterilized or disinfected. The shape of some of the catheter components makes it difficult for light to reach all points on the surface of catheter 15 and skin 3 near entrance site 11, where the catheter is placed against the skin. The catheter may create a partially shadowed area that receives less light than other areas. The effects of shadowing may be mitigated if the total dosage of sterilizing light is high enough. However, a higher dosage requires a more powerful UV light source and/or a greater exposure time, which may cause a greater UV exposure to the skin than desired. Accordingly, in one embodiment of the invention, the components of the catheter are shaped to reduce shadowing and/or include light reflecting or refracting components to direct light to areas that might otherwise be partially or fully shadowed.

Referring again to FIG. 2, catheter 15 is shown illuminated with light source 7. As shown, an area 38 of skin 3 under the portion of catheter 15 is ordinarily not exposed to light from light source 7 due to shadowing by catheter 15. Reflector 9 causes light emitted by light source 7 to approach the target surfaces and objects from a multitude of different angles. Thus, some light will reach partially shadowed area 38, but the total intensity of the light striking area 38 will be less than that of the surrounding areas. Additional reflectors or diffusers may be used to further increase the intensity of the light striking area 38.

Figure 6A:
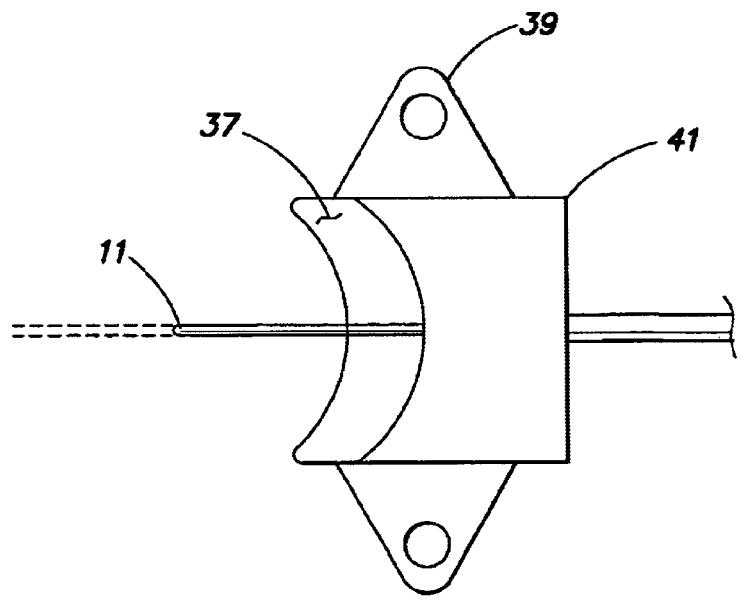
FIGS. 6A–6B illustrate a light directing component for use with a sterilization/disinfection unit.
Figure 6B:
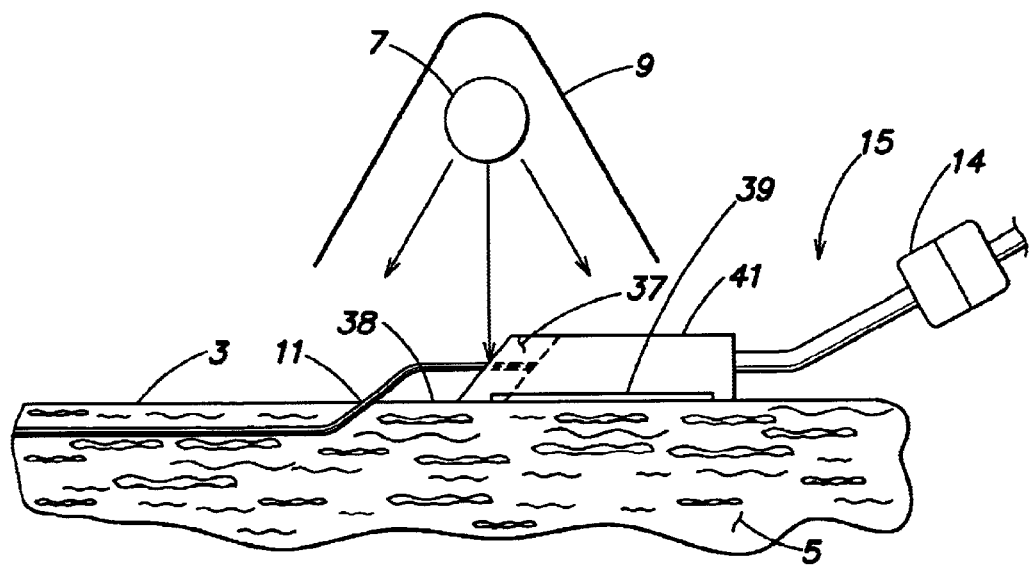

FIG. 6B illustrates an example of how catheter components may be shaped to direct light to partially shadowed area 38 for more uniform light distribution. In this example, a reflective surface 37 is included on a light directing component 41 to reflect light from light source 7 to partially shadowed area 38. Light directing component 41 may be the hub of catheter 15, as shown in FIG. 6B, or may be an additional component, as will be described in connection with FIG. 7A. Thus, light directing component 41 may be an existing portion of catheter 15 or a component added to catheter 15. Reflective surface 37 may be a sloped and/or mirrored, as shown in FIGS. 6A and 6B. Although a curved mirror is shown, one or more planar mirrors or refractive optics such as a cylindrical lens made of a UV transparent material, may be used to direct the light from light source 7 to area 38 under catheter 15.

Tabs 39 may be provided on either side of light directing component 41 to provide a mechanism for attaching light directing component 41 to the patient. For example, tabs may be affixed to tissue 5 using sutures or an adhesive. The upper surface of light directing component 41 may be shaped in a smooth arch to provide a better light seal with instantaneous sterilization/disinfection unit 16a, as shown in FIGS. 7A, 7B, and 7C.

Figure 7A:
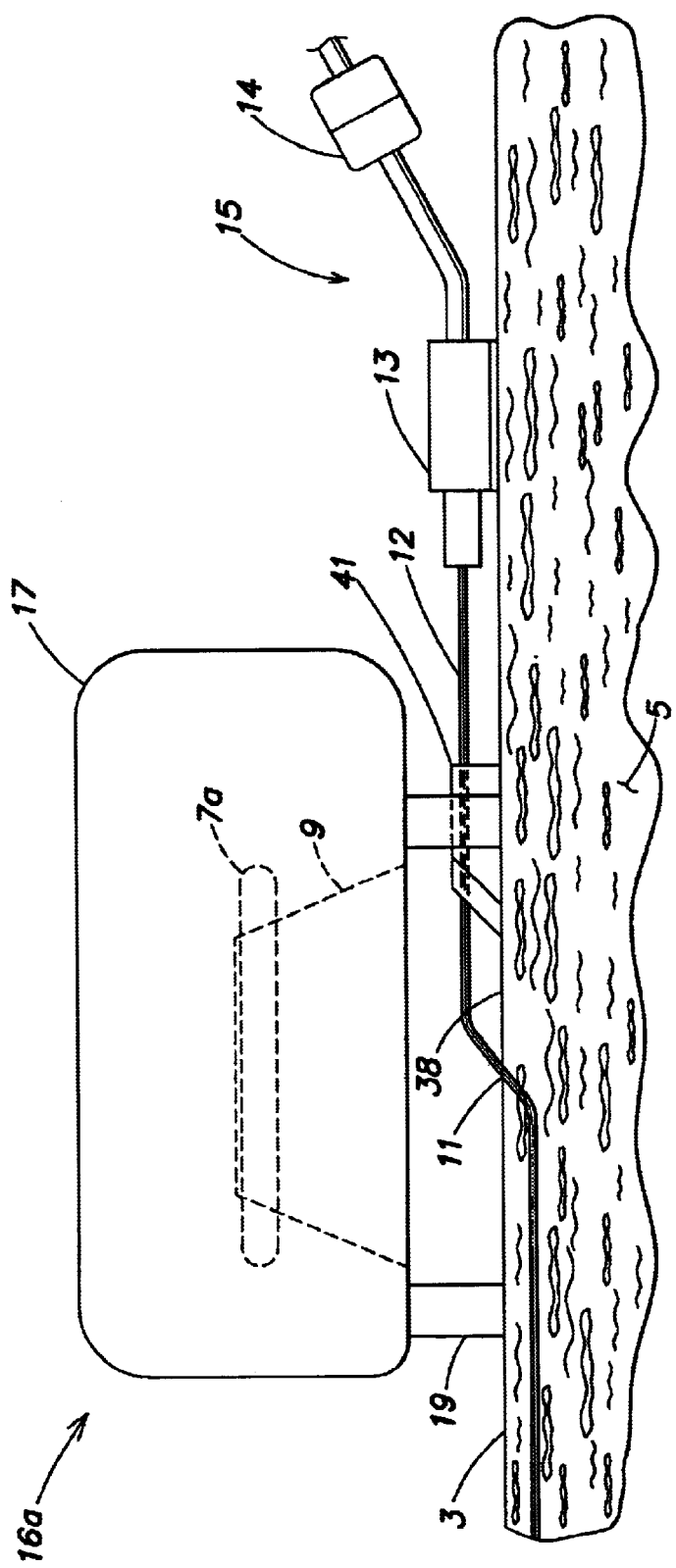
FIGS. 7A–7C illustrate the light directing component of FIGS. 6A–6B used with the instantaneous sterilization/disinfection unit of FIGS. 3 and 4A–4E.
Figure 7B:
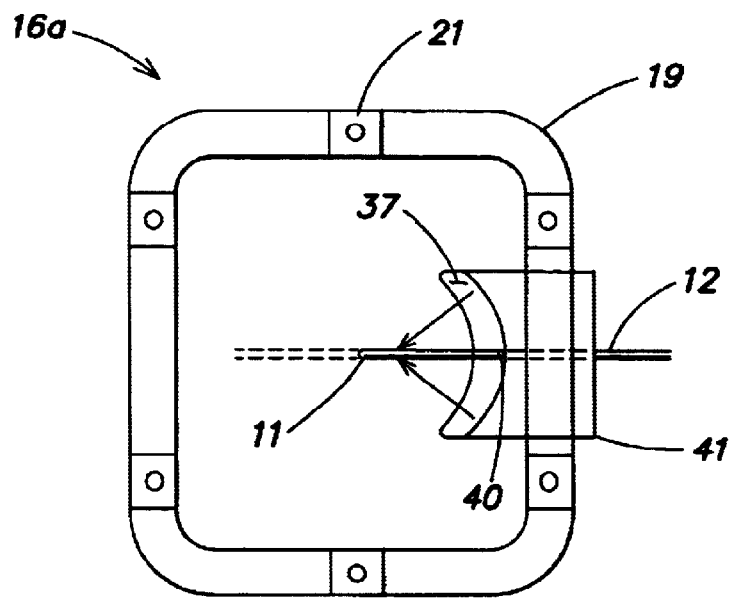
Figure 7C:
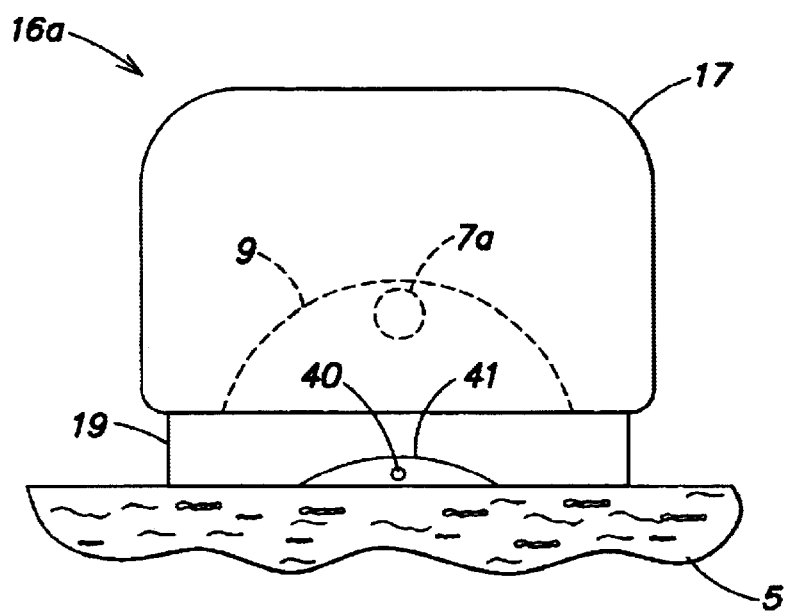

FIGS. 7A, 7B, and 7C illustrate light directing component 41 used with instantaneous sterilization/disinfection unit 16a. It should be appreciated that while instantaneous sterilization/disinfection unit 16a is illustrated, other sterilization/disinfection devices such as continuous process sterilization/disinfection unit 16b may alternatively be used in this embodiment. In some catheter installations, hub 13 is not positioned close enough to entrance site 11 for reflective surface 37 to perform the desired function of directing light to area 38 if reflective surface 37 is attached to hub 13. Thus, in this embodiment, light directing component 41 is separate from hub 13. Light-directing component 14 may attach to tube 12 of catheter 15 and may be movable along tube 12 so that it may be positioned near entrance site 11 after catheter 15 is installed. Further, light directing component 41 may have adhesive to hold light directing component 41 in place once it is positioned on skin 3. Preferably, light directing component 41 holds tube 12 of catheter 15 slightly above the surface of skin 3 to allow sterilizing light to reach the skin under tube 12. FIGS. 7A, 7B, and 7C show catheter 15 passing through a hole 40 in light directing component 41, but alternatively the component could have a groove to accommodate tube 12 of catheter 15. Light directing component 41 may be molded from plastic, an elastomer, or a photochromic plastic or elastomer. Alternatively, light directing component 41 may include a color-changing additive that changes color upon exposure to UV light. A color-changing effect may provide verification to an operator that the target site has been exposed to UV light.

Light directing component 41 may not include reflective surface 37. In this case, the light directing component 41 may still hold tube 12 of catheter 15 away from skin 3 to allow sterilizing light to reach area 38. If the dispersion of the light from instantaneous sterilization/disinfection unit 16a is high enough, partially shadowed area 38 may receive enough sterilizing light from the unit without the use of a specific reflective surface. As above, light directing component 41 without reflective surface 37 may include photochromic indicators to indicate an exposure to UV light.

Sterilization/disinfection units 16a and 16b are designed to have a beneficial effect when used with the standard catheters and installation techniques currently in common use. However, alterations to the physical configuration of the catheter and the positioning of external catheter components may improve the ease of use and efficacy of sterilization/disinfection units 16. These alterations include adding to or changing the shape of the external catheter components to minimize shadowing and/or to enhance the light seal of the sterilization/disinfection unit, or adding color-changing materials to indicate UV light exposure.

UV-Transmissive Bandage

The sterilization/disinfection units previously described are also designed to have a beneficial effect when used on bare skin, and they may be used with traditional bandages if the bandage is temporarily removed for the exposure to the sterilizing light. However, in accordance with an embodiment of the invention, the method for sterilization or disinfection described herein may be implemented with a UV-transmissive bandage in place over the region to be sterilized/disinfected. The term bandage is intended to include any dressing, medical tape, pad, gauze, film, ointment, or paint-on wound covering, or any combination of features thereof.

Bandages that transmit sterilizing or disinfecting light may be made by choosing appropriate materials and configurations. For example, materials that are typically considered opaque to UVC light may transmit a significant percentage of UVC light when fabricated as a thin film. For example, a thin film of polyethylene (a common material used for medical applications) having a thickness of 0.002 inches (0.05 mm) transmits up to 80% of sterilizing light from a xenon flash having a wavelength in the range of 220 to 310 nm. Even films up to 0.01 inches (0.25 mm) thick may transmit over 50% of the sterilizing light. Adhesive tapes including a structural film and adhesive with a total thickness of 0.006 inches (0.15 mm) may have a transmission of sterilizing light of greater than 60%. A typical eight-layer thick medical gauze pad transmits about 30% of the sterilizing light.

Medical bandages for use with catheters often consist only of a layer of visually transparent tape with a layer of adhesive added. Many of the visually transparent films currently used are nearly opaque to light with a wavelength shorter than 310 nm and are unsuitable for UV light transmission. However, bandages may be fabricated from a specific material in an appropriate thickness to enhance UV transmission. For example, bandages fabricated from hydrophilic polyurethane sheet material with a thickness of approximately 0.001 inch (0.025 mm) and with a film of acrylic based adhesive with a thickness of approximately 0.001 inch (0.025 mm), as described in U.S. Pat. No. 4,595,001, may have a transmission of sterilizing light that is greater than 50%. This transmissivity is acceptable for sterilization of disinfection through the bandage. A bandage for use with a sterilization/disinfection unit may be manufactured to have a known and controlled transmissivity to UV light. Thus, the light output of the sterilization/disinfection unit may be adjusted to deliver the correct dosage of sterilizing light to the skin and catheter components to be sterilized or disinfected.

Figure 8:
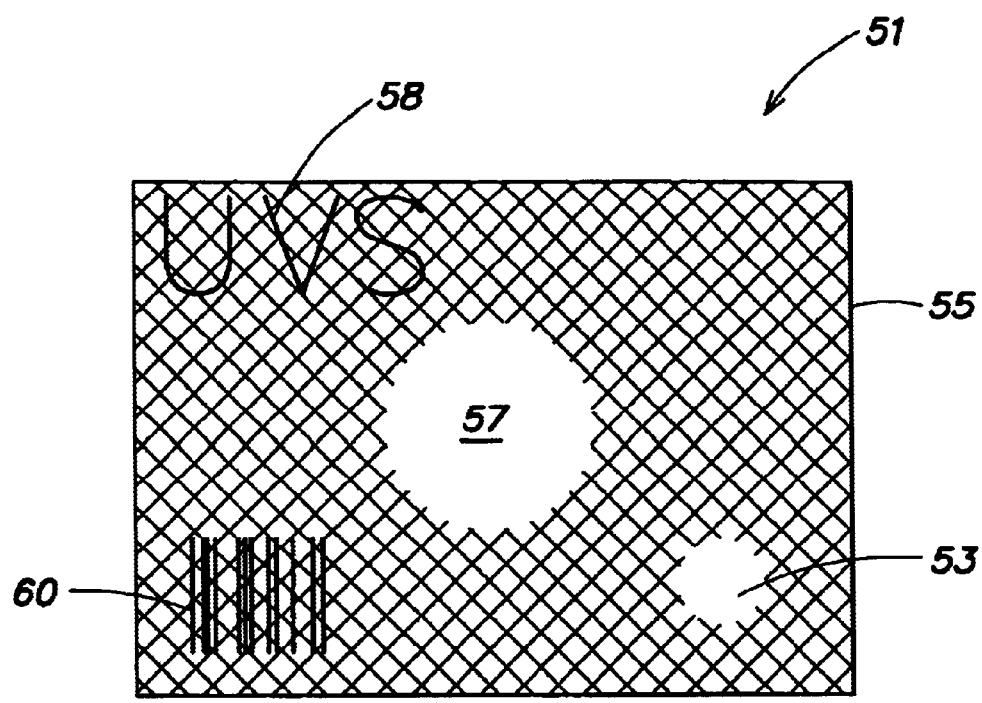
FIG. 8 illustrates a first embodiment of a UV-transmissive bandage.

FIG. 8 illustrates a first configuration of a bandage 51 designed for use with a sterilization/disinfection unit, as described herein. As shown, bandage 51 has an adhesive 53 coupled to the periphery of a film 55 of bandage 51. Adhesive 53 may attenuate UV light and therefore reduce the amount of light that reaches the skin. To minimize this attenuation, adhesive 53 in bandage 51 of FIG. 8 is selectively applied such that the portion of film 55 that is placed above the entrance site of the catheter is free of adhesive 53. Adhesive 53 forms a seal around the periphery of bandage 51, which will provide a barrier to microbes. Since UV light applied to the bandage may pass through region 57 of bandage 51, which does not contain adhesive 53, the UV transmission characteristics of adhesive 53 are not critical and do not need to be controlled in manufacture.

All of the bandages described herein may be enhanced with additional features to facilitate their use with a sterilization/disinfection unit. In one example, a radiant heat attenuating material may be added to film 55 of bandage 51 to attenuate any heat generated by the UV light source. In another example, a color-changing material, such as a photochromic or fluorescent ink or dye may be added to adhesive 53 or film 55 of bandage 51. The color-changing material may change color or emit light when exposed to UV light. Alternatively, the color-changing material may change color or emit light when exposed to light from another portion of the spectrum. A color change resulting from light from another portion of the spectrum may still provide an indication of UV light exposure if the proportion of UV light to the light from the other portion of the spectrum is known.

Since color-changing material may absorb some of the UV light applied, and therefore reduce UV transmission, color-changing material may be included only in a portion or portions of bandage 51, as desired. For example, color-changing material may be applied to adhesive 53 or film 55 discontinuously, e.g., in a pattern. The pattern may be an array of lines, dots, or other small shapes, to allow the UV light to sterilize or disinfect the areas between the color-changing material. Alternatively, color-changing material may be applied along the edge of bandage 51 so as to not interfere with the application of UV light. In yet another alternative, for bandages that are larger than the illuminated area of the sterilization/disinfection unit, a small amount of color-changing material may be added to the entire bandage. While the addition of the color-changing material to the entire bandage may decrease the UV light transmission of bandage 51 by a small amount, the bandage will transmit a sufficient amount of UV light as long as the total transmission of the bandage is known and the light output is adjusted accordingly.

As discussed above, color-changing material may be added to adhesive 53. For example, color-changing material may be included in adhesive 53 to make adhesive-free region 57 more obvious and, hence, easier to position. Another additive, other than a color-changing material, may alternatively be included to achieve easier positioning. Color-changing material may also be included in adhesive 53 to indicate that a sterilization/disinfection operation has successfully occurred.

Also as discussed above, color-changing material may be added to film 55. For example, color-changing material may also be included in or printed onto film 55 of bandage 51 to indicate a region or level of exposure of bandage 51 to UV light. In another example, color-changing material may be included in or printed onto film 55 of bandage 51 in a meaningful pattern to convey information. As shown in FIG. 8, color-changing material may be printed to form a logo 58, or other word or icon, or a barcode 60. Color-changing material may also be printed to provide additional information or instructions to a user or indicate a manufacturer of the product.

A color-changing material having a long time constant (i.e., a slow color response) may also be added to film 55 of bandage 51. The relaxation time constant for the color-changing material may be chosen to match the desired time between doses of UV light from a sterilization/disinfection unit. For example, when exposed to a UV light dose, the color-changing material may change to match a background color, making the color-changing material nearly invisible. As the color-changing material changes back to its original color, the material becomes more visible. When a user is able to detect the color-changing material, or a pattern formed by the material, the user may determine that reapplication of UV light is appropriate. Alternatively, an optical detection device (e.g., a photodetector) may be included in a sterilization/disinfection unit to detect a pattern or hue of the color-changing material, where a hue detected may include a color, brightness, saturation, or presence or absence of coloration of the color-changing material. For example, a pattern of color-changing material may form barcode 60, detectable by an optical detection device. The sterilization/disinfection unit may be designed to operate only when the barcode, or other pattern or hue, is readable.

Sterilization/disinfection unit may include a sensor to detect if it is being used on bare skin or a bandage. One way of sensing the material is to measure the electrical conductivity of its surface by making electrical connection with two or more contact points of the surface and measuring the resistance between the points. Human skin will typically have a resistance of less than a few megaohms, whereas the materials used for a bandage will typically be hundreds of times higher. The conductivity may also be measured using capacitive coupling and an alternating current sense signal to measure the coupling between the contact points. If a sterilization/disinfection unit detects that it is applied to bare skin, the output level of its light source may be adjusted to a level appropriate for bare skin.

The bandage detection feature may be used alone, or in combination with a feature that automatically detects and adjusts the output of the light source for different bandage types. For example, if the unit detects the presence of a bandage, a photosensor or other sensor may be activated to detect a code that appears on the bandage. The code may be, for example, a barcode printed on the edge of the bandage. The barcode may indicate the UV light transmission characteristics of the bandage so that the sterilization/disinfection unit may adjust its output accordingly. A sterilization/disinfection unit with this feature would need to be positioned properly to be operated, which would encourage proper use. The sterilization/disinfection unit may include operator indicators to inform the operator when the unit is properly positioned and the code may be read. Indicators may also be provided to inform the operator as to what intensity is being selected, or if more than one application is required for proper sterilization or disinfection through the bandage. This feature may be combined with the long time constant color-changing material used for the barcode to prevent the application of UV light more frequently than is required.

Bandages that include pads (like those sold commercially under the tradename "Band-Aid," and larger varieties used in professional medicine) may also be constructed in a manner that allows sufficient sterilizing light transmission for use with a sterilization/disinfection unit. The pad provides greater flexibility, which results in more comfortable bandages and improved adhesion to the body. The pad may be made from a foamed polyethylene or similar material with significant transmission of UV light. For best transmission of UV light, the material would not have colorants added, but would be a clear or milky color. However, colorants that do not significantly degrade the transmission of UV light, versus visible light, may be used.

Figure 9A:
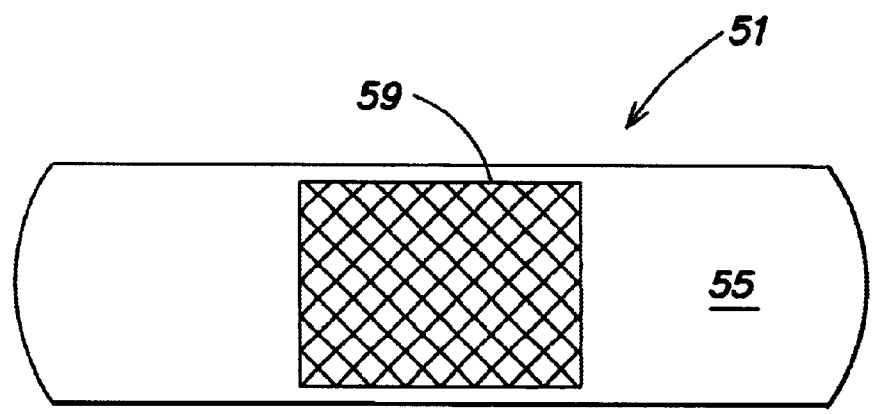
FIGS. 9A–9B illustrate another embodiment of a UV-transmissive bandage.
Figure 9B:
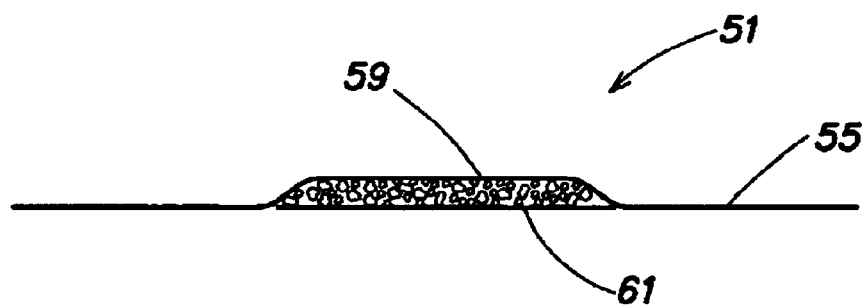

FIGS. 9A and 9B illustrate another configuration of a bandage designed for use with a sterilization/disinfection unit, as described herein. In this configuration, bandage 51 has a pad 59 coupled to film 55 of the bandage, and a pad liner 61 coupled to pad 59. Pad 59 and pad liner 61 are sufficiently transmissive to UV light. The adhesive on film 55 also preferably is sufficiently transmissive to UV light in the thickness used. A variety of adhesives meet this condition, including some currently used for medical bandages and dressings. The adhesive on pad liner 61 holds pad 59 in position and adheres film 55 to the user's skin.

For sufficient UV light transmission, pad 59 should be made from an appropriate UV transmissive material and be made in an appropriate thickness. The pads of typical prefabricated bandages are in the range of 0.02 inch (0.5 mm) to 0.06 inch (1.5 mm) thick and are fabricated of medical gauze or a non-woven (felt-like) fabric. Some bandages include a perforated polymeric sheet liner on the pad, as shown in FIG. 9B.

A UV transmissive bandage may be made with traditional materials if no colorants are used in the film (as is typical). For example, the pad may be made from 8 layers of medical gauze (approximately 0.04 inch (1 mm) thick), and the pad liner may be made from a 0.002 inch (0.05 mm) thick polyethylene sheet. In an exemplary bandage, the film with adhesive may have a sterilizing light transmission of 75%, the pad may have a sterilizing light transmission of 30%, and the liner may have a sterilizing light transmission of about 80%. This would result in a total sterilizing light transmission of about 18%. Although a higher transmission of sterilizing light is desirable, it is still possible to use a bandage of this construction in connection with the sterilization and disinfection methods described herein. Sterilizing or disinfecting the surface of the skin through this bandage would require a total sterilizing/disinfecting light dosage of about 5.5 times that required for bare skin.

One exemplary alternative for the bandage described above is to substitute a foamed polyethylene pad for a gauze pad. A foamed polyethylene pad with a thickness of 0.04 inch (1 mm) may have a sterilizing light transmission of 70%. The foamed pad presents a polymeric surface to the wound, so a pad liner is not required. A bandage made in this configuration has a total sterilizing light transmission of about 50%, requiring only twice the sterilizing light intensity required by bare skin. This configuration has the advantage of requiring less energy from the sterilization/disinfection unit, though there may be medical reasons why a configuration with a fabric pad is preferable. Both configurations may be used with an appropriately designed sterilization/disinfection unit.

Figure 10A:
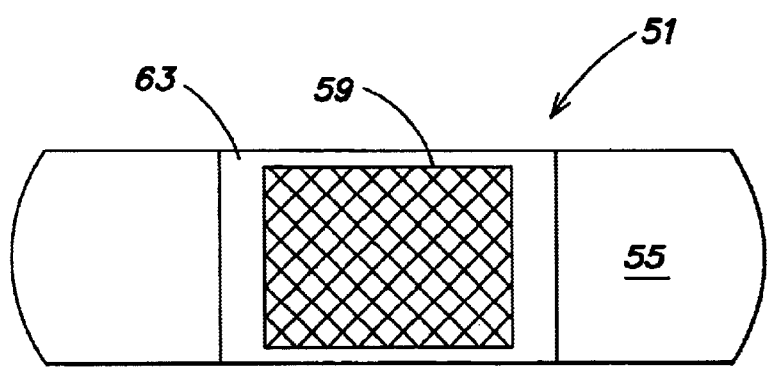
Figure 10B:
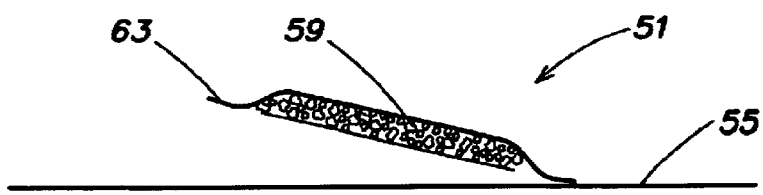
Figure 10C:
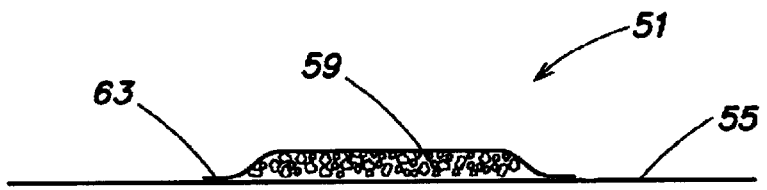

FIGS. 10A, 10B, and 10C illustrate a further configuration of a bandage designed for use with a sterilization/disinfection unit, as described herein. In this configuration, film 55 is used in place of pad liner 61 of the configuration of FIG. 9B. Film 55 may be perforated at the position of pad 59 if it is desired for fluids to flow into the pad. Pad 59 is attached to film 55 with a movable fastening 63. The fastening may be an adhesive fastener or hook and loop fasteners, commonly know as "Velcro." Pad 59 may be completely removed or folded to one side. Thus, UV light from a sterilization/disinfection unit may reach the skin of the user without traversing pad 59. Since the UV transmission characteristics of pad 59 are not critical in this configuration, the pad thickness and material may be determined based on medical considerations. Hence, thick gauze pads are possible. Further, in this configuration, the underside of pad 59 may be sterilized or disinfected when the pad is totally or partially disengaged from film 55. Thus, pad 59 may be sterilized or disinfected during use to created a sterile surface.

The materials and/or colorants used in the bandages described herein may be chosen and positioned such that the attenuation of the sterilizing light through the bandage is similar for all portions of the bandage. This allows a sterilizing dose of UV light to be applied to the bandage without having some areas of the skin underneath the bandage overdosed, which could cause damage to the skin. For example, to achieve uniform attenuation of the sterilizing light, the section of film 55 of bandage 51 that does not cover pad 59 may be made to provide greater attenuation of the sterilizing light than film 55 covering pad 59 to compensate for the extra attenuation of pad 59. The light attenuation of the film may be controlled by printing film 55 with a colored ink or dye that absorbs, blocks or reflects the sterilizing light. Alternatively, the adhesive will normally provide some attenuation to the sterilizing light and its thickness and/or composition may be controlled so the attenuation matches that of the pad. If the pad is as large or larger than the illuminated area of the wound sterilizer/disinfector, then the UV transmission characteristics of the adhesive tape beyond the extent of the pad may not be relevant.

Since one of the side effects of the application of UV light to the skin is a suntan, it may be desirable to fabricate the bandage to make the tanned spot less obvious by feathering the edges. This may be done by grading the UV transmissivity of the bandage to successively lower values towards the edges of the illuminated area. This would cause any suntan to have a gradual edge, rather that a shape edge that would be more noticeable and displeasing. The plastic film in the tape or bandage could also include an additive that selectively absorbs or blocks the transmission of some wavelengths of light to alter the spectrum of light that reaches the skin to filter out harmful or undesired wavelengths. This filter could also reduce the suntan effect.

Figure 11A:
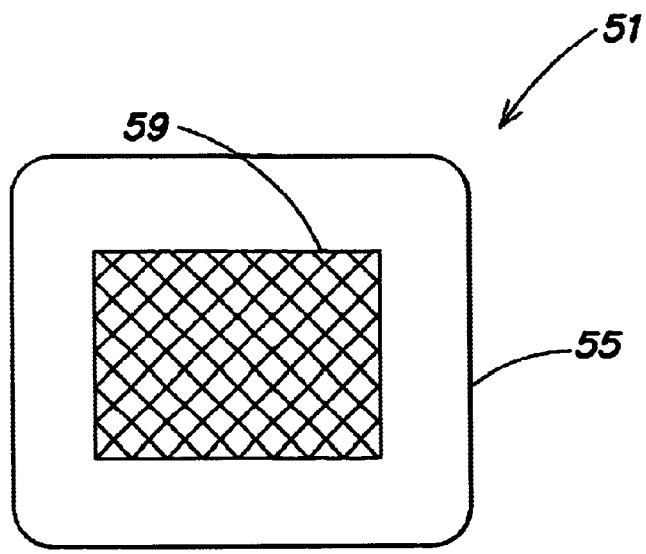
FIGS. 11A–11B illustrate another embodiment of a UV-transmissive bandage.
Figure 11B:
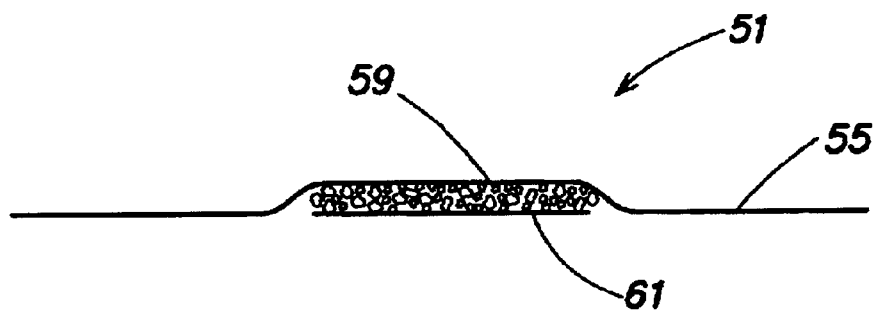

The bandages described herein may be used for many different professional and consumer health care applications. FIGS. 11A and 11B illustrate another configuration of a bandage designed for use with a sterilization/disinfection unit, as described herein. The bandage of this configuration is typically a larger bandage for use in professional applications. Bandage 51 includes a substantially square film 55 with a substantially square pad 59 attached thereto. This configuration has the advantage that a secure airtight seal maybe formed on the complete periphery of bandage 51, which may create a complete barrier to external infection by microorganisms. Bandages with this property may be manufactured in a variety of sizes and shapes for professional medical use, consumer use, and veterinary medical use. Catheters and regions of skin may be sterilized or disinfected with one of the described sterilization/disinfection units before and/or after the bandage is applied, and periodically with the bandage in place, either by medical professionals or by consumers.

Sterilization or Disinfection Using a UV-Transmissive Bandage

Figure 12:
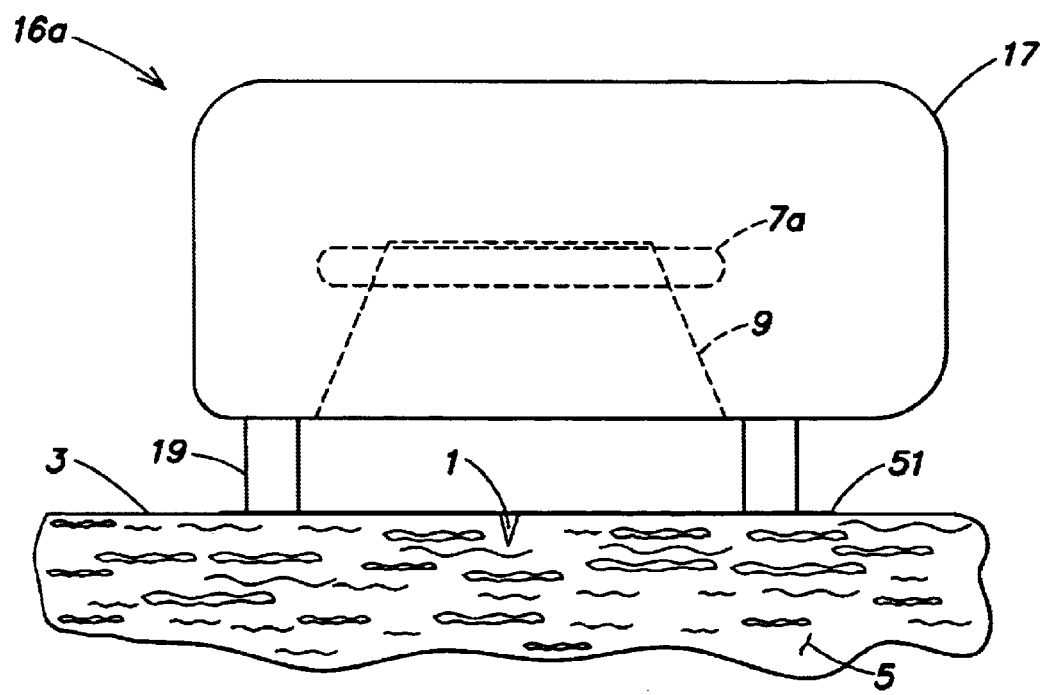
FIG. 12 illustrates the instantaneous sterilization/disinfection unit of FIGS. 3 and 4A–4E used with a UV-transmissive bandage.

FIG. 12 illustrates the instantaneous sterilization/disinfection unit 16a of FIGS. 3–4 used with a UV-transmissive bandage 51. For illustrative purposes, bandage 51 is shown covering wound 1. However, bandage 51 may alternatively or additionally cover a catheter, a catheter entrance site, or healthy skin. FIG. 13 illustrates the continuous process sterilization/disinfection unit 16b of FIGS. 5A, 5B, and 5C used with bandage 51. Similarly, while bandage 51 is shown covering wound 1, it may alternatively or additionally cover a catheter, a catheter entrance site, or healthy skin.

Figure 13:
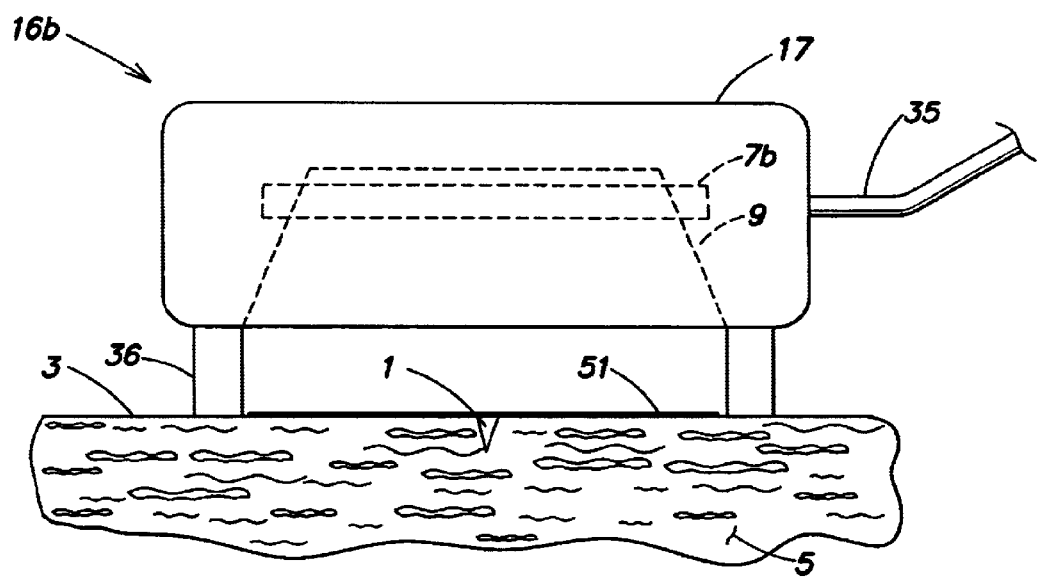
FIG. 13 illustrates the continuous process sterilization/disinfection unit of FIGS. 5A–5C used with a UV-transmissive bandage.

Bandage 51 of FIGS. 12 and 13 may include any of the features or materials described herein, and is not limited to any of the particular configurations described. As discussed, sterilization/disinfection units 16a and 16b may generate UV light at an intensity matched to the UV transmissivity of bandage 51. The light intensity generated by sterilization/disinfection units 16a and 16b may be variable by means of a knob, switch, or other mechanism on the units. The UV transmissivity of bandage 51 may be measured by a user or may be indicated, e.g., on the bandage itself. An indication on bandage 51 may be detectable by a sensor, e.g., a photosensor, within sterilization/disinfection units 16a and 16b. Color-changing material coupled to the underside of bandage 51 may indicate an absorption of UV light and, hence, a transmissivity of bandage 51.

Although it is not necessary, bandage 51 may form a seal to prevent contamination of the bandaged site. For example, the bandage may be formed of a continuous film that is impervious to microorganisms, such as bacteria and viruses. Existing commercially available bandages may have UV-transmissive properties, although they are not intended to be used in sterilization or disinfection operations that use ultraviolet light. Thus, this incidental property of commercially available bandages makes them suitable for use with the described sterilization/disinfection units 16a and 16b.

It is preferable to use bandages with controlled UV transmission characteristics so as to achieve consistent results. Bandages with controlled UV transmission characteristics may be made using conventional manufacturing processes with additional quality control of the materials and thickness used. As discussed previously, additives may be used on or in the film, pad, or adhesive of the bandage used with sterilization/disinfection units 16a and 16b to control UV transmission or block harmful or undesirable wavelengths of light.

Sterilization or Disinfection Using a Light Directing Component and a Bandage

Figure 14A:
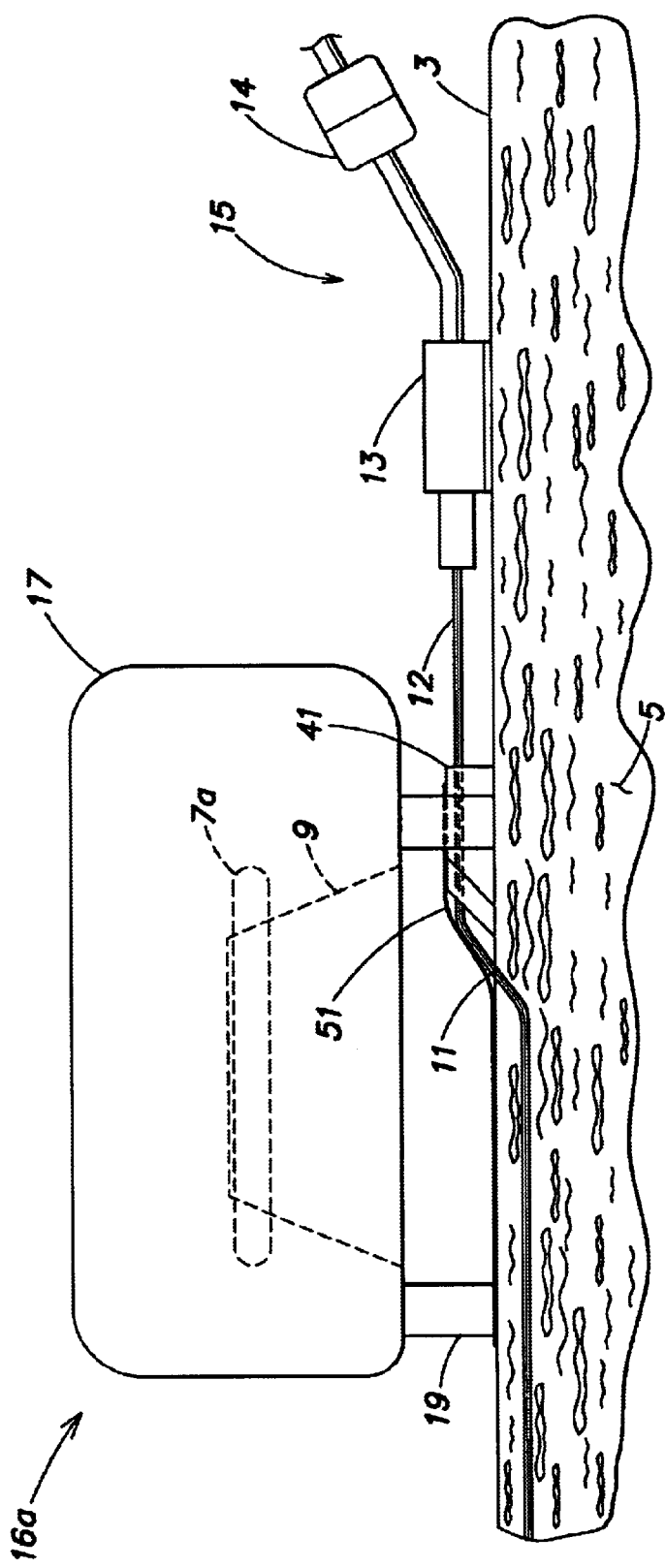
FIGS. 14A–14C illustrate the instantaneous sterilization/disinfection unit of FIGS. 3 and 4A–4E used with the light directing component of FIGS. 6A–6B and a UV transmissive bandage.
Figure 14B:
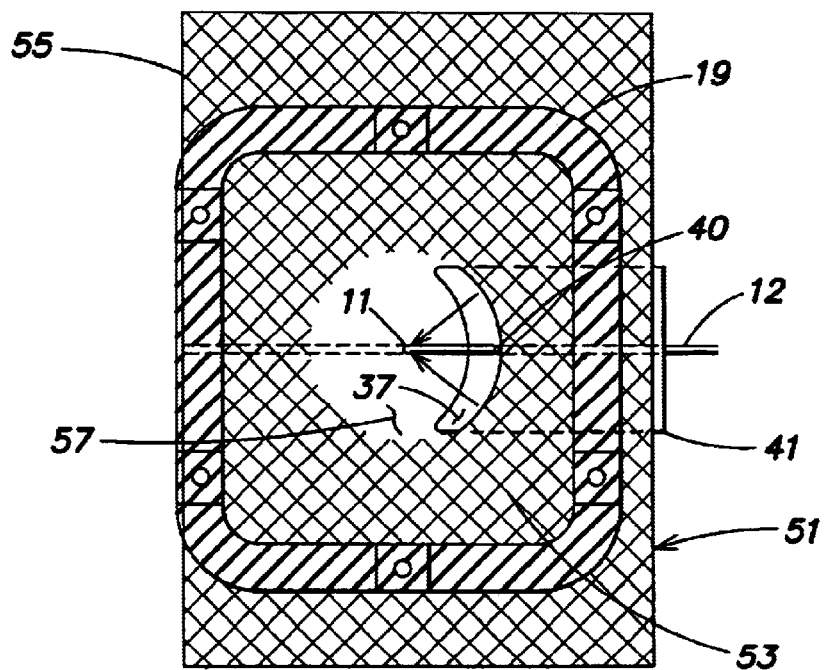
Figure 14C:
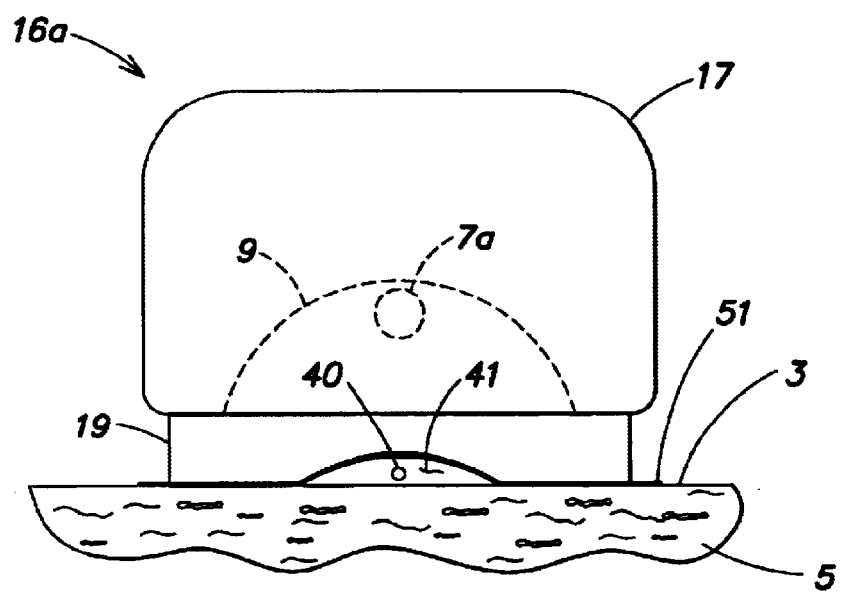

FIGS. 14A, 14B, and 14C illustrate light directing component 41 and instantaneous sterilization/disinfection unit 16a of FIGS. 7A, 7B, and 7C used with bandage 51. It should be appreciated that while instantaneous sterilization/disinfection unit 16a is illustrated, other sterilization/disinfection devices such as continuous process sterilization/disinfection unit 16b may alternatively be used in this embodiment. When used with bandage 51, light directing component 41 may form an air seal with tube 12 of catheter 15 and bandage 51 to prevent contamination of entrance site 11 by external microbes carried by air. Light directing component 41 may assist in forming this air seal by providing a smooth convex curved surface over catheter 15, as shown in FIG. 14C, to which bandage 51 is easily adhered. Without light directing component 41, it would be difficult for bandage 51 to form a complete seal between skin 3 and the underside of tube 12 of catheter 15.

FIG. 14B illustrates a bandage 51 having a film 55 partially coated with an adhesive 53. A region 57 of film 55 above catheter entrance site 11 is not coated with adhesive 53. Region 57 without adhesive 53 is used to secure catheter 15 while providing an ability to sterilize or disinfect entrance site 11 and the surrounding region by transmitting UV light through bandage 51. In the example of FIG. 14B, region 57 without adhesive 53 is large enough to allow the UV light to sterilize or disinfect an area around entrance site 11 and allow the UV light to reach light directing component 41 to assure proper illumination under tube 12 of catheter 15. Adhesive 53 forms a seal with skin 3 and light directing component 41 to prevent entrance site 11 from being infected from external microbes.

It should be appreciated that adhesive 53 need not be applied to bandage 51 of FIG. 14B in the illustrated way, according to the invention. For example, region 57, which does not contain adhesive 53, may be larger or smaller, or shaped differently. Further, region 57 may be eliminated altogether so that adhesive 53 is applied continuously, intermittently, in rows, in dots, or in any other type of pattern.

To form a complete air seal, light directing component 41 is designed to have intimate contact with tube 12 of catheter 15. This may be achieved in a variety of ways, such as molding the light directing component 41 from an elastomer so that it forms a tight fit over tube 12, forming a groove in light directing component 41 that has a hinged or separate piece to fill at least part of the groove, using a rigid light directing component 41 with an inserted elastomeric seal, using the elastomeric properties of the catheter 15 to seal against a rigid light directing component 41, or forming a seal with the addition of an adhesive material around tube 12 of catheter 15.

Reflective surface 37 of light directing component 41 may be a separate attached component or it may be integral with light directing component 41. The light directing function of light directing component 41 may be separated from the light and/or air sealing function of light directing component 41 and one or more separate components may be used. It should be appreciated that while a number of example configurations are described to perform the functions of light directing, light sealing and air sealing, those skilled in the art will readily see a variety of other configurations that may perform these function in various combinations.

Because the underside of hub 13 and/or light-directing component 41 is not exposed to light, it is not sterilized once in position. However, is not necessary to repeatedly sterilize this area as the skin under hub 13 and/or light directing component 41 is intact and provides an appropriate barrier to microorganisms. Skin 3 and tube 12 of catheter 15 in the vicinity of entrance site 11 need to be periodically sterilized/disinfected to prevent microorganisms from entering the body at entrance site 11. If the area around entrance site 11 is periodically sterilized or disinfected, and non-sterile objects or air do not come in contact with this area, the body is protected from infection entering through the entrance site 11.

Sterilization or Disinfection of a Sterilization/Disinfection Unit

The sterilization/disinfection units described herein may be used for multiple patients in a professional medical environment. The sterilization/disinfection unit itself could become a vector to transmit microorganisms for one patient to another. In particular, a bottom surface 48 of light seal 19, which is not normally exposed to UV light, may come in contact with a patient, a catheter, or a bandage.

Figure 15:
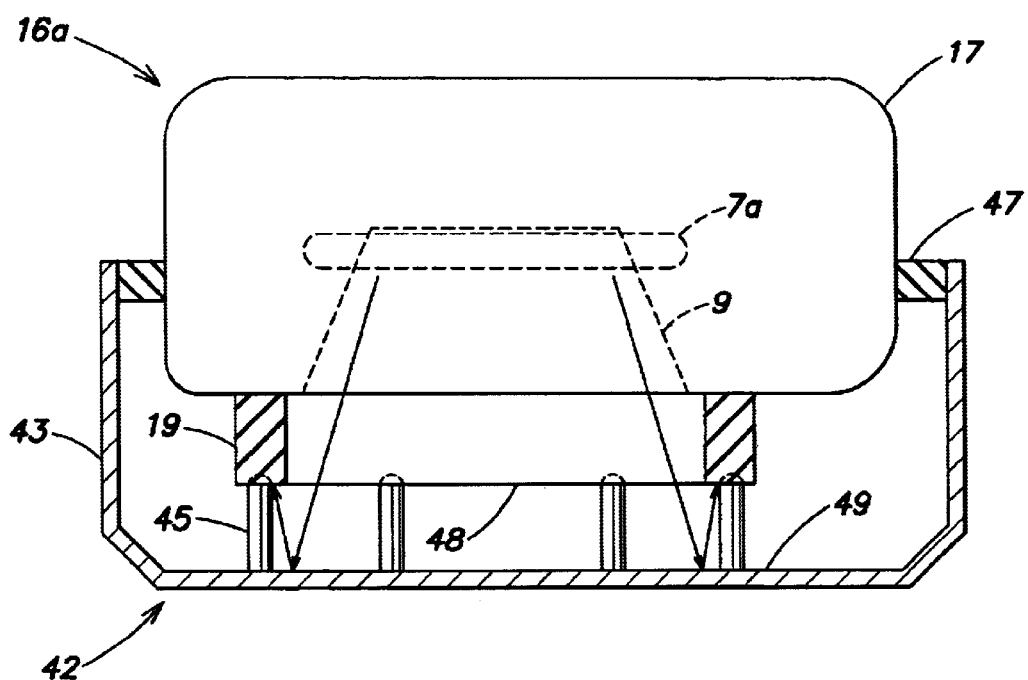
FIG. 15 illustrates a self-sterilizing attachment coupled to the instantaneous sterilization/disinfection unit of FIGS. 3 and 4A–4E.

FIG. 15 illustrates an example embodiment of a self-sterilizer attachment 42 for instantaneous sterilization/disinfection unit 16a. Self-sterilizer attachment 42 includes a housing 43, into which instantaneous sterilization/disinfection unit 16a may be placed. A light seal 47, disposed on the inner rim of housing 43, forms a seal with instantaneous sterilization/disinfection unit 16a when the unit is positioned within housing 43. Light seal 47 may be compliant, and substantially prevents light from escaping from housing 43 when instantaneous sterilization/disinfection unit 16a is in use. Self-sterilizer attachment 42 includes pins 45 at the base of housing 43. Pins 45 may be UV-transmissive to allow the region on light seal 19 that contacts the pins to be sterilized or disinfected. When light seal 19 of instantaneous sterilization/disinfection unit 16a contacts and/or depresses pins 19, safety interlock actuators in light seal 19 of instantaneous sterilization/disinfection unit 16a are activated. The activation may engage instantaneous sterilization/disinfection unit 16a in a "ready mode," which allows an operator to trigger generation of light by light source 7, e.g., by pressing a trigger switch on the unit. Alternatively, activation of the actuators may automatically cause instantaneous sterilization/disinfection unit 16a to emit light.

Housing 43 includes one ore more reflective surfaces 49. Reflective surfaces 49 direct light to bottom surface 48 of light seal 19, the underside of unit 16a, and/or the exterior of housing 17 of unit 16a. Reflective surfaces 49 may be formed of aluminum, mirrors, or another UV-light reflective surface. When light is emitted by instantaneous sterilization/disinfection unit 16a, reflective surfaces 49 direct light back towards the unit to cause sterilization or disinfection of its surfaces. More than one flash or dose may be applied for an increased UV light dosage to ensure complete sterilization, as there are typically no objects present within housing 43 that would be damaged by a higher exposure.

It should be appreciated that although instantaneous sterilization/disinfection unit 16a is shown, self-sterilizer may be used with any of the sterilization/disinfection units described herein. Further, although self-sterilizer attachment 42 is shown as an attachment to the sterilization/disinfection unit, alternatively it may be integrated therewith. Although pins 45 are shown and described as activating the actuators, a number of alternative configurations may be used to perform the same function (e.g., a light detector, a mechanical lever, a magnetic field detector, or a pressure sensor).

Electrical Configuration of an Instantaneous Sterilization/Disinfection Unit

Figure 16:
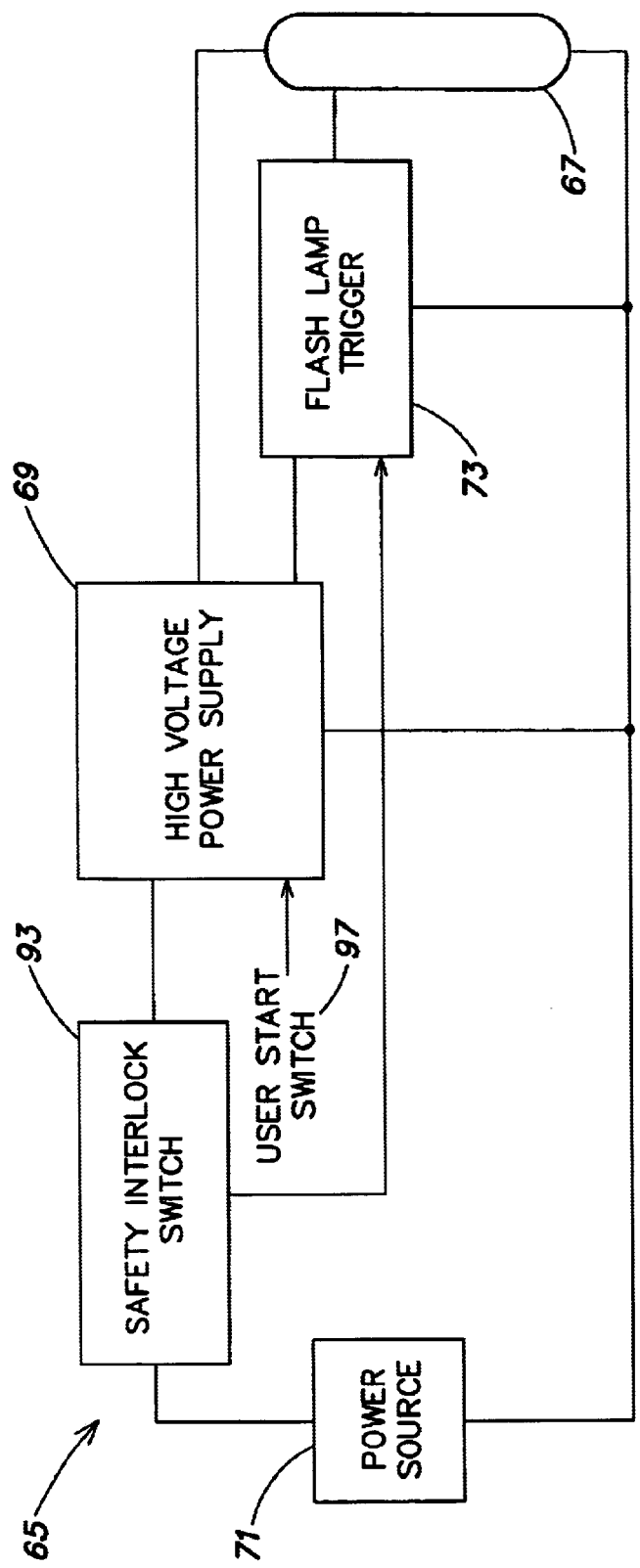
FIG. 16 illustrates a block diagram of exemplary circuitry for use in the instantaneous sterilization/disinfection unit of FIGS. 3 and 4A–4E.

According to one embodiment of the invention, electrical circuitry associated with a flash lamp of an instantaneous sterilization/disinfection unit 16a may be implemented as shown by electrical circuit 65 in FIG. 16. Electrical circuit 65 may be used in a sterilization/disinfection unit according to any of the embodiments described above. Electrical circuit 65 uses a high voltage power supply 69 that contains a capacitor to store the energy necessary to power a flash lamp 67. A power source 71, which may be an AC line or a battery, typically supplies a voltage in the range of 200V to 1000V depending characteristics of the flash lamp used, although the voltage supplied may be smaller than 200V or greater than 1000V. Small linear flash lamps typically operate with voltages of 200V to 500V; small short-arc flash lamps may require 1000V or more. The voltage is selected based on the flash lamp specifications: the total energy desired per flash and the maximum flash current desired. A higher voltage will provide a higher flash current for the same energy, resulting in a greater percentage of the flash light output in the ultraviolet spectrum. The energy per flash is determined by Equation 1:

$$E = \tfrac{1}{2}CV^2 \quad [1]$$

where E is the energy per flash in Joules, C is the value of the energy storage capacitor in Farads and V is the voltage in volts. For a sterilizer/disinfector application, the selected voltage should be as high as possible so that the flash lamp produces the greatest amount of ultraviolet light. The value of the capacitor is then chosen to provide the desired amount of energy per flash. The energy required by the flash to perform the sterilization/disinfection is determined by the amount of area to be illuminated, the minimum sterilizing light dosage desired, the uniformity of the illumination, and the spectrum of flash lamp 67. For example, a flash lamp made from UV glass used to illuminate 25 square centimeters (about 4 square inches) produces a UVC energy intensity of about 20 mJ/cm$^2$ with a total flash input energy of about 20 joules.

The sterilizer/disinfector circuitry also includes a flash lamp trigger 73 which is very similar to the trigger circuit in a camera flash. The flash lamp trigger provides a very high voltage pulse, typically in the range of 4 kV to 15 kV depending on the specifications of the flash lamp, to initiate the flash. According to one embodiment of the sterilizer/disinfector, a charge storage capacitor is kept charged to the appropriate voltage whenever the unit is powered on. Safety interlock switch 75 may prevent triggering of flash lamp 67 when the a light seal formed by sterilization/disinfection unit 16a is incomplete. Thus, flash lamp trigger 73 may be initiated when a trigger switch and a safety interlock switch 75 have been activated. Alternatively, either trigger switch (e.g., a pushbutton) or safety interlock switch 75 (e.g., mechanical actuators) may individually initiate flash lamp trigger 73.

Figure 17:
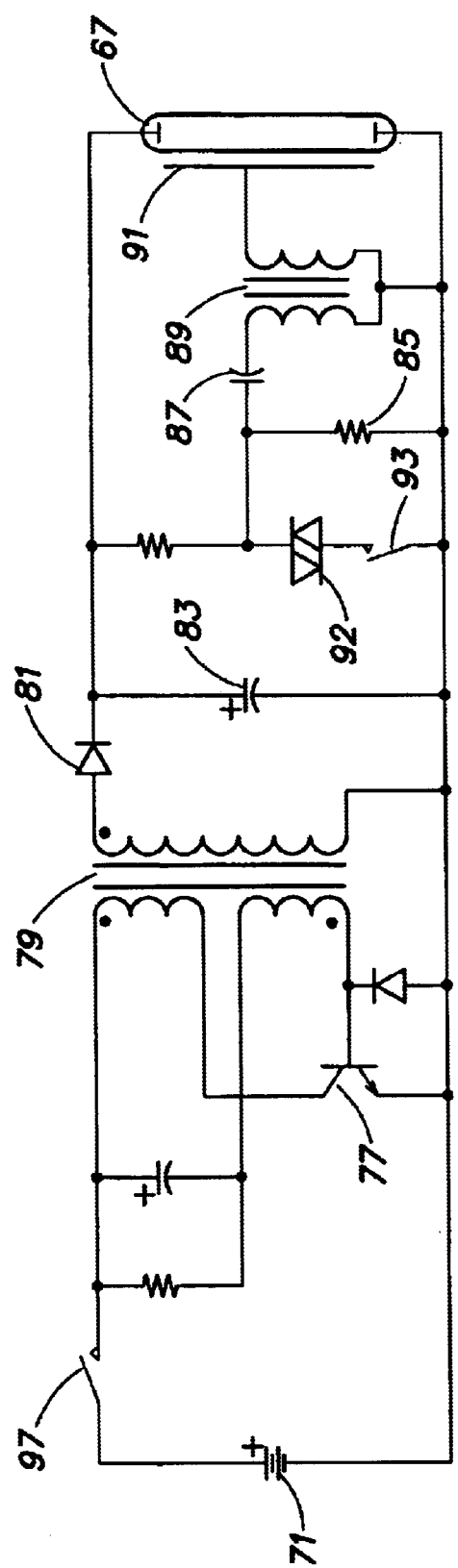
FIG. 17 illustrates a schematic diagram of exemplary circuitry for use in the instantaneous sterilization/disinfection unit of FIGS. 3 and 4A–4E.

FIG. 17 shows one example of a typical battery powered xenon flash lamp driver circuit with trigger circuitry for activating flash lamp 67. Circuits of this nature are commonly used in camera flash units. For simplicity, the diagram does not show the details of an AC power supply or user indicators. A power transistor 77 and its related components form a low voltage oscillator, typically in the range of 15 to 20 kHz. Current from a high voltage transformer 79 passes through a high voltage diode 81 and charges an energy storage capacitor 83 to a voltage that will drive flash lamp 67. A resistor 85 charges a trigger capacitor 87 to the flash lamp voltage. When a diac 92 and a safety interlock switch 93 are turned-on, trigger capacitor 87 is discharged through a trigger transformer 89 which creates a very high voltage pulse to a trigger electrode 91 on flash lamp 67 This causes flash lamp 67 to flash using the stored energy in energy storage capacitor 83.

It should be appreciated that the above-described circuitry is merely intended to illustrate one possible implementation, and many such circuits are possible and known in the art. For example, there exists in the art many circuits for driving flash lamps that may be suitably applied to the sterilizers/disinfectors described herein. Thus, the invention is not limited in this respect.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and equivalents thereto.

What is claimed is:

1. A method of sterilizing or disinfecting a region underneath a bandage on a patient, comprising an act of:
   applying ultraviolet light to the region through the bandage, wherein the act of applying ultraviolet light includes applying ultraviolet light to a portion of a catheter underneath the bandage.

2. A method of sterilizing or disinfecting a region underneath a bandage on a patient, comprising acts of:
   applying ultraviolet light to the region through the bandage; and
   detecting an exposure of at least a portion of the bandage to ultraviolet light.

3. The method of claim 2, wherein the act of detecting an exposure of the at least a portion of the bandage to ultraviolet light includes detecting a hue in a portion of the bandage.

4. The method of claim 3, wherein the act of detecting an exposure of the at least a portion of the bandage to ultraviolet light includes using a optical detection device to detect the hue.

5. The method of claim 4, wherein the act of applying occurs only when the optical detection device detects a particular hue.

6. The method of claim 2, wherein the act of detecting an exposure of the at least a portion of the bandage to ultraviolet light includes detecting a pattern in a portion of the bandage.

7. The method of claim 6, wherein the act of detecting an exposure of the at least a portion of the bandage to ultraviolet light includes using a optical detection device to detect the pattern.

8. The method of claim 7, wherein the act of applying occurs only when the optical detection device detects a particular pattern.

9. A system for sterilizing or disinfecting a region of tissue of a patient, comprising:
   an ultraviolet light-emitting lamp; and
   a bandage adapted to transmit at least some of the ultraviolet light emitted by the lamp;

wherein the bandage covers at least a portion of the region of tissue; and wherein the bandage includes a movable pad.

10. A system for sterilizing or disinfecting a region of tissue of a patient, comprising:

an ultraviolet light-emitting lamp; and a bandage adapted to transmit at least some of the ultraviolet light emitted by the lamp;

wherein the bandage covers at least a portion of the region of tissue; and wherein the bandage includes a light filter to filter a chosen portion of a light spectrum emitted by the ultraviolet light-emitting lamp.

11. A method, comprising acts of:

determining the transmissivity of at least a portion of a bandage to ultraviolet light; and selecting an intensity of ultraviolet light to be applied through at least a portion of the bandage.

12. The method of claim 11, wherein the act of determining the transmissivity of the at least a portion of the bandage to ultraviolet light includes reading a visual indicator on the bandage.

13. The method of claim 12, wherein the act of determining the transmissivity of the at least a portion of the bandage to ultraviolet light includes reading a barcode on the bandage.

14. A bandage, comprising:

an ultraviolet light-transmissive film; and a color-changing material coupled to the film to indicate an exposure of the film to ultraviolet light.

15. The bandage of claim 14, wherein an adhesive coupled to the film includes the color-changing material.

16. The bandage of claim 14, wherein the color-changing material is chosen such that a duration of time required for the color-changing material to revert to a state present prior to an application of ultraviolet light corresponds with a desired duration of time between applications of ultraviolet light.

17. The bandage of claim 14, wherein the color-changing material is embedded in the film.

* * * * *